US011447834B2

(12) United States Patent
Abebe et al.

(10) Patent No.: US 11,447,834 B2
(45) Date of Patent: Sep. 20, 2022

(54) **GENETIC ARRAY FOR SIMULTANEOUS DETECTION OF MULTIPLE *SALMONELLA* SEROVARS**

(71) Applicant: Tuskegee University, Tuskegee, AL (US)

(72) Inventors: Woubit Abebe, Tuskegee, AL (US); Khaled Aldhami, Tuskegee, AL (US); Sayma Afroj, Tuskegee, AL (US); Temesgen Samuel, Tuskegee, AL (US); Gopal Reddy, Tuskegee, AL (US)

(73) Assignee: TUSKEGEE UNIVERSITY, Tuskegee, AL (US)

( * ) Notice: Subject to any disclaimer, the term of this patent is extended or adjusted under 35 U.S.C. 154(b) by 379 days.

(21) Appl. No.: 16/431,039

(22) Filed: Jun. 4, 2019

(65) Prior Publication Data

US 2020/0017904 A1    Jan. 16, 2020

Related U.S. Application Data

(60) Provisional application No. 62/680,351, filed on Jun. 4, 2018.

(51) Int. Cl.
*C12Q 1/689*     (2018.01)
*B01L 3/00*      (2006.01)

(52) U.S. Cl.
CPC .......... *C12Q 1/689* (2013.01); *B01L 3/50851* (2013.01); *B01L 2300/0829* (2013.01); *C12Q 2561/101* (2013.01); *C12Q 2600/16* (2013.01)

(58) Field of Classification Search
CPC ................ C12Q 1/689; C12Q 2600/16; C12Q 2561/101; B01L 3/50851; B01L 2300/0829
See application file for complete search history.

(56) References Cited

U.S. PATENT DOCUMENTS

2008/0124712 A1 * 5/2008 Hantash ............... C12Q 1/6883
435/5

OTHER PUBLICATIONS

Afroj et al. Simultaneous detection of multiple *Salmonella* serovars from milk and chicken meat by real-time PCR using unique genomic target regions. Journal of Food Protection 2017; 80: 1944-1957. (Year: 2017).*
Gen Bank Accession No. NC_021810 for *Salmonella enterica* subsp. enterica serovar Heidelberg str. 41578, complete sequence, Nov. 9, 2020 [online], [retrieved on Sep. 4, 2021], retrieved from the Internet: <URL: www.ncbi.nlm.nih.gov/nuccore/NC_021810>. (Year: 2020).*
Malorny et al. Polymerase Chain Reaction for the Rapid Detection and Serovar Identification of *Salmonella* in Food and Feeding Stuff. Food Analytical Methods 2009; 2: 81-95. (Year: 2009).*
Bolotin et al. Development of a novel real-time reverse-transcription PCR method for the detection of H275Y positive influenza A H1N1 isolates. Journal of Virological Methods 2009; 158: 190-194. (Year: 2009).*
Hadjinicolaou et al. Molecular beacon-based real-time PCR detection of primary isolates of *Salmonella typhimurium* and *Salmonella enteritidis* in environmental and clinical samples. BMC Microbiology 2009; 9: 97 + Additional File 1 (Year: 2009).*
Balamurugan, V., K. D. Jayappa, M. Hosamani, V. Bhanuprakash, G. Venkatesan, and R. K. Singh. 2009. Comparative efficacy of conventional and TaqMan polymerase chain reaction assays in the detection of capripoxviruses from clinical samples. Journal of veterinary diagnostic investigation. 21:225-231.
Becker, L., M. Steglich, S. Fuchs, G. Werner, and U. Nübel. 2016. Comparison of six commercial kits to extract bacterial chromosome and plasmid DNA for MiSeq sequencing. Scientific Reports. 6:28063.
Braden, C. R. 2006. *Salmonella enterica* serotype Enteritidis and eggs: a national epidemic in the United States. Clin Infect Dis. 43:512-7.
Bugarel, M., A. Tudor, G. H. Loneragan, and K. K. Nightingale. 2017. Molecular detection assay of five *Salmonella* serotypes of public interest: Typhimurium, Enteritidis, Newport, Heidelberg, and Hadar. J Microbiol Methods 134:14-20.
CDC. 1984. *Salmonella* Dublin and raw milk consumption California. MMWR. 33:196-8.
CDC. 2003. *Salmonella* Surveillance Summary, 2002. In US Depailment of Health and Human Services (ed.) CDC, Atlanta, Georgia.
CDC. 2014. Notes from the Field: Multistate Outbreak of Human *Salmonella* Infections Linked to Live Poultry from a Mail-Order Hatchery in Ohio Mar.-Sep. 2013 p. 222 In, MMWR, vol. 63.
Cernela, N., M. Nuesch-Inderbinen, H. Hächler, and R. Stephan. 2014. Antimicrobial resistance patterns and genotypes of *Salmonella enterica* serovar Hadar strains associated with human infections in Switzerland, 2005-2010. Epidemiology and infection. 142:84-89.
Chen, J., L. Zhang, G. C. Paoli, C. Shi, S.-I. Tu, and X. Shi. 2010. A real-time PCR method for the detection of *Salmonella enterica* from food using a target sequence identified by comparative genomic analysis. International journal of food microbiology. 137:168-174.
Chikami, G. K., J. Fierer, and D. G. Guiney. 1985. Plasmid-Mediated Virulence in *Salmonella* Dublin Demonstrated by Use of a Tn5-oriT Construct American Society for Microbiology. 50:420-424.

(Continued)

*Primary Examiner* — Angela M. Bertagna
(74) *Attorney, Agent, or Firm* — Terry M. Sanks, Esq.; Beusse Sanks, PLLC

(57) ABSTRACT

Disclosed are novel genetic arrays for use in the molecular detection of multiple *Salmonella* serovars, common food-borne and water-borne pathogens. The arrays may be used to simultaneously detect multiple food safety *Salmonella* serovars. The multiplex-detection methods have improved sensitivity and specificity for the detection of multiple high-impact food-borne pathogens simultaneously. Real-time PCR assaying techniques using such serovars include microarrays.

4 Claims, 6 Drawing Sheets

(6 of 6 Drawing Sheet(s) Filed in Color)

Specification includes a Sequence Listing.

(56) References Cited

OTHER PUBLICATIONS

Chu, C., Y. Feng, A.-C. Chien, S. Hu, C.-H. Chu, and C.-H. Chiu. 2008. Evolution of genes on the *Salmonella* Virulence plasmid phylogeny revealed from sequencing of the virulence plasmids of *S. enterica* serotype Dublin and comparative analysis. Genomics. 92:339-343.
Demczuk, W., G. Soule, C. Clark, H.-W. Ackermann, R. Easy, R. Khakhria, F. Rodgers, and R. Ahmed. 2003. Phage-based typing scheme for *Salmonella enterica* serovar Heidelberg, a causative agent of food poisonings in Canada. Journal of clinical microbiology. 41:4279-4284.
Dietz, H. H., M. Chriél, T. H. Andersen, J. C. Jorgensen, M. Torpdahl, H. Pedersen, and K. Pedersen. 2006. Outbreak of *Salmonella* Dublin-associated abortion in Danish fur farms. Canadian veterinary journal. 47:1201.
Dinjus, U., I. Hänel, W. Müller, R. Bauerfeind, and R. Helmuth. 1997. Detection of the induction of *Salmonella enterotoxin* gene expression by contact with epithelial cells with RT-PCR. FEMS microbiology letters. 146:175-179.
Doran, J. L., S. K. Collinson, C. M. Kay, P. A. Banser, J. Burian, C. K. Munro, S. H. Lee, J. M. Somers, E. C. Todd, and W. W. Kay. 1994. fimA and tctC based DNA diagnostics for *Salmonella*. Mol Cell Probes. 8:291-310.
Dupont, H. L. 2007. The growing threat of foodborne bacterial enteropathogens of animal origin. Clinical infectious diseases. 45:1353-1361.
Ebersbach, G., and K. Gerdes. 2005. Plasmid segregation mechanisms. Annu Rev Genet. 39:453-79.
Fakruddin, M., K. S. B. Mannan, and S. Andrews. 2013. Viable but Nonculturable Bacteria: Food Safety and Public Health Perspective. ISRN Microbiology. 2013:6.
Ferretti, R., Mannazzu, I, Cocolin, Luca, Comi, Giuseppe, & Clementi, Francesca. . 2001. Twelve-hour PCR-based method for detection of *Salmonella* spp. in food. Applied and environmental microbiology. 67(2) 977-978.
Fricke, W. F., P. F. McDermott, M. K. Mammel, S. Zhao, T. J. Johnson, D. A. Rasko, P. J. Fedorka-Cray, A. Pedroso, J. M. Whichard, J. E. LeClerc, D. G. White, T. A. Cebula, and J. Ravel. 2009. Antimicrobial Resistance-Conferring Plasmids with Similarity to Virulence Plasmids from Avian Pathogenic *Escherichia coli* Strains in *Salmonella enterica* Serovar Kentucky Isolates from Poultry. Applied and Environmental Microbiology. 75:5963-5971.
Gillespie, B., and S. Oliver. 2005. Simultaneous detection of mastitis pathogens, *Staphylococcus aureus*, *Streptococcus uberis*, and *Streptococcus agalactiae* by multiplex real-time polymerase chain reaction. Journal of dairy science. 88:3510-3518.
Grant, M. A., J. Hu, and K. C. Jinneman. 2006. Multiplex real-time PCR detection of heat-labile and heat-stable toxin genes in enterotoxigenic *Escherichia coli*. Journal of Food Protection®. 69:412-416.
Greene, H., and D. Dempsey. 1986. Bovine neonatal salmonellosis: An outbreak in a dairy calf rearing unit. Irish Veterinary Journal. 40:30-34.
Guard, J., R. Sanchez-Ingunza, C. Morales, T. Stewart, K. Liljebjelke, J. Van Kessel, K. Ingram, D. Jones, C. Jackson, P. Fedorka-Cray, J. Frye, R. Gast, and A. Hinton, Jr. 2012. Comparison of dkgB-linked intergenic sequence ribotyping to DNA microarray hybridization for assigning serotype to *Salmonella enterica*. FEMS Microbiol Lett. 337:61-72.
Guo, X., J. Chen, L. R. Beuchat, and R. E. Brackett. 2000. PCR Detection of *Salmonella enterica*Serotype Montevideo in and on Raw Tomatoes Using Primers Derived from hilA. Applied and environmental microbiology 66:5248-5252.
Hadjinicolaou, A. V., V. L. Demetriou, M. A. Emmanuel, C. K. Kakoyiannis, and L. G. Kostrikis. 2009. Molecular beacon-based real-time PCR detection of primary isolates of *Salmonella typhimurium* and *Salmonella enteritidis* in environmental and clinical samples. BMC Microbiol. 9:97.
Hohmann, E. L. 2001. Nontyphoidal salmonellosis. Clin Infect Dis. 32:263-9.
Hoorfar J, C. N., Malorny B, Wagner M, De Medici D, Abdulmawjood A, Fach P. 2004. Diagnostic PCR: making internal amplification control mandatory. J Appl Microbiol. 96(2).
Jackson, B. R., P. M. Griffin, D. Cole, K. A. Walsh, and S. J. Chai. 2013. Outbreak-associated *Salmonella enterica* serotypes and food Commodities, United States, 1998-2008. Emerg Infect Dis 19:1239-44.
Kim, H., S. Park, T. Lee, B. Nahm, Y. Chung, K. Seo, and H. Kim. 2006. Identification of *Salmonella enterica* serovar Typhimurium using specific PCR primers obtained by comparative genomics in *Salmonella* serovars. Journal of Food Protection®. 69:1653-1661.
Kim, H.-J., S.-H. Park, T.-H. Lee, B.-H. Nahm, Y.-R. Kim, and H.-Y. Kim. 2008. Microarray detection of food-borne pathogens using specific probes prepared by comparative genomics. Biosensors and Bioelectronics. 24:238-246.
Kimura, A. C., V. Reddy, R. Marcus, P. R. Cieslak, J. C. Mohle-Boetani, H. D. Kassenborg, S. D. Segler, F. P. Hardnett, T. Barrett, and D. L. Swerdlow. 2004. Chicken consumption is a newly identified risk factor for sporadic *Salmonella enterica* serotype Enteritidis infections in the United States: a case-control study in FoodNet sites Clinical Infectious Diseases. 38:S244-S252.
Kingsley, R. A., and A. J. Bäumler. 2000. Host adaptation and the emergence of infectious disease: the *Salmonella* paradigm. Molecular microbiology. 36:1006-1014.
Krause, M., and D. G. Guiney. 1991. Identification of a multimer resolution system involved in stabilization of the *Salmonella* dublin virulence plasmid pSDL2. Journal of Bacteriology. 173:5754-5762.
Kubota, K., E. Iwasaki, S. Inagaki, T. Nokubo, Y. Sakurai, M. Komatsu, H. Toyofuku, F. Kasuga, F. J. Angulo, and K. Morikawa. 2008. The human health burden of foodborne infections caused by Campylobacter, *Salmonella*, and Vibrio parahaemolyticus in Miyagi Prefecture, Japan. Foodborne Pathog Dis. 5:641-8.
Lampel, K., S. Keasler, and D. Hanes. 1996. Specific detection of *Salmonella enterica* serotype Enteritidis using the polymerase chain reaction. Epidemiology and infection. 116:137-145.
Le Hello, S., A. Bekhit, S. A. Granier, H. Barua, J. Beutlich, M. Zajac, S. Munch, V. Sintchenko, B. Bouchrif, K. Fashae, J. L. Pinsard, L. Sontag, L. Fabre, M. Garnier, V. Guibert, P. Howard, R. S. Hendriksen, J. P. Christensen, P. K. Biswas, A Cloeckaert, W. Rabsch, D. Wasyl, B. Doublet, and F. X. Weill. 2013. The global establishment of a highly-fluoroquinolone resistant *Salmonella enterica* serotype Kentucky ST198 strain. Front Microbiol. 4:395.
Le Hello, S., D. Harrois, B. Bouchrif, L. Sontag, D. Elhani, V. Guibert, K. Zerouali, and F. X. Weill. 2013. Highly drug-resistant *Salmonella enterica* serotype Kentucky ST198-X1: a microbiological study. Lancet Infect Dis. 13:672-9.
Le Hello, S., R. S. Hendriksen, B. Doublet, I. Fisher, E. M. Nielsen, J. M. Whichard, B. Bouchrif, K. Fashae, S. A. Granier, N. Jourdan-Da Silva, A. Cloeckaert, E. J. Threlfall, F. J. Angulo, F. M. Aarestrup, J. Wain, and F.-X. Weill. 2011. International Spread of an Epidemic Population of *Salmonella enterica* Serotype Kentucky ST198 Resistant to Ciprofloxacin. Journal of Infectious Diseases.
Liu, Z. M., X. M. Shi, and F. Pan. 2007. Species-specific diagnostic marker for rapid identification of *Staphylococcus aureus*. Diagn Microbiol Infect Dis. 59:379-82.
Majowicz, S. E., J. Musto, E. Scallan, F. J. Angulo, M. Kirk, S. J. O'Brien, T. F. Jones, A. Fazil, and R. M. Hoekstra. 2010. The global burden of nontyphoidal *Salmonella* gastroenteritis. Clinical Infectious Diseases. 50:882-889.
Malorny, B., C. Bunge, and R. Helmuth. 2007. A real-time PCR for the detection of *Salmonella* Enteritidis in poultry meat and consumption eggs. J Microbiol Methods. 70, pp. 245-251.
Malorny, B., J. Hoorfar, C. Bunge, and R. Helmuth. 2003. Multicenter validation of the analytical accuracy of *Salmonella* PCR: towards an international standard. Applied and environmental microbiology. 69:290-296.
Malorny, B., E. Paccassoni, P. Fach, C. Bunge, A. Martin, and R. Helmuth. 2004. Diagnostic real-time PCR for detection of *Salmonella* in food Appl Environ Microbiol. 70:7046-52.
Marcus, R., J. Varma, C. Medus, E. Boothe, B. Anderson, T. Crume, K. Fullerton, M. Moore, P. White, and E. Lyszkowicz. 2007.

(56) References Cited

OTHER PUBLICATIONS

Re-assessment of risk factors for sporadic *Salmonella* serotype Enteritidis infections: a case-control study in five FoodNet Sites, 2002-2003. Epidemiology and Infection. 135:84-92.

Mateus, A., D. J. Taylor, D. Brown, D. J. Mellor, R. Bexiga, and K. Ellis. 2008. Looking for the unusual suspects: a *Salmonella* Dublin outbreak investigation. Public Health. 122:1321-3.

Maurischat, S., B. Baumann, A. Martin, and B. Malorny. 2015. Rapid detection and specific differentiation of *Salmonella enterica* subsp. enterica Enteritidis, Typhimurium and its monophasic variant 4,[5], 12: i:—by real-time multiplex PCR. International journal of food microbiology. 193:8-14.

Murugkar, H. V., H. Rahman, and P. K. Dutta. 2003. Distribution of virulence genes I *Salmonella* serovars isolated from man & animals. Indian J Med Res. 117:66-70.

Nielsen, L. R., B. van den Borne, and G. van Schaik. 2007. *Salmonella* Dublin infection in young dairy calves: transmission parameters estimated from field data and an SIR-model. Prev Vet Med. 79:46-58.

O'Regan, E., E. McCabe, C. Burgess, S. McGuinness, T. Barry, G. Duffy, P. Whyte, and S. Fanning. 2008. Development of a real-time multiplex PCR assay for the detection of multiple *Salmonella* serotypes in chicken samples. BMC microbiology. 8:156.

Ou, H. Y., C. T. Ju, K. L. Thong, N. Ahmad, Z. Deng, M. R. Barer, and K. Rajakumar. 2007. Translational genomics to develop a *Salmonella enterica* serovar Paratyphi A multiplex polymerase chain reaction assay. J Mol Diagn. 9:624-30.

Pullinger, G. D., and A. J. Lax. 1992. A *Salmonella* Dublin virulence plasmic locus that affects bacterial growth under nutrient-limited conditions. Molecular Microbiology. 6:1631-1643.

Raghunathan, A., H. R. Ferguson, Jr., C. J. Bomarth, W. Song, M. Driscoll, and R. S. Lasken. 2005. Genomic DNA amplification from a single bacterium. Appl Environ Microbiol. 71:3342-7.

Sint, D., L. Raso, and M. Traugott. 2012. Advances in multiplex PCR: balancing primer efficiencies and improving detection success. Methods in Ecology and Evolution 3:898-905.

Sivapalasingam, S., C. R. Friedman, L. Cohen, and R. V. Tauxe. 2004. Fresh produce: a growing cause of outbreaks of foodborne illness in the United States, 1973 through 1997. Journal of Food Protection®. 67:2342-2353.

Song, J.-H., H. Cho, M. Y. Park, Y. S. Kim, H. B. Moon, Y. K. Kim, and C. H. Pai. 1994. Detection of the H1-j strain of *Salmonella typhi* among Korean isolates by the polymerase chain reaction. The American journal of tropical medicine and hygiene. 50:608-611.

Uzzau, S., D. J. Brown, T. Wallis, S. Rubino, G. Leori, S. Bernard, J. Casadesús, D. J. Platt, and J. E. Olsen. 2000. Host adapted serotypes of *Salmonella enterica*. Epidemiology and infection. 125:229-255.

Vandegraaff, R., and J. Malmo. 1977. *Salmonella* Dublin in dairy cattle. Australian veterinary journal. 53:453-455.

Voetsch, A. C., T. J. Van Gilder, F. J. Angulo, M. M. Farley, S. Shallow, R. Marcus, P. R. Cieslak, V. C. Deneen, R. V. Tauxe, and G. Emerging Infections Program FoodNet Working. 2004. FoodNet estimate of the burden of illness caused by nontyphoidal *Salmonella* infections in the United States. Clin Infect Dis. 38 Suppl 3:S127-34.

Wattam, A. R., J. J. Davis, R. Assaf, S. Boisvert, T. Brettin, C. Bun, N. Conrad, E. M. Dietrich, T. Disz, J. L. Gabbard, S. Gerdes, C. S. Henry, R. W. Kenyon, D. Machi, C. Mao, E. K. Nordberg, G. J. Olsen, D. E. Murphy-Olson, R. Olson, R. Overbeek, B. Parrello, G. D. Pusch, M. Shukla, V. Vonstein, A. Warren, F. Xia, H. Yoo, and R. L. Stevens. 2017. Improvements to PATRIC, the all-bacterial Bioinformatics Database and Analysis Resource Center. Nucleic Acids Res. 45:D535-D542.

Woubit, A. S., T. Yehualaeshet, T. Habtemariam, and T. Samuel. 2012. Simultaneous, specific and real-time detection of biothreat and frequently encountered food-borne pathogens. Journal of food protection. 75:660-670.

Wray, C., and W. J. Sojka. 1977. Bovine salmonellosis. Journal of Dairy Research. 44:383-425.

Yarmolinsky, M. B. 1995. Programmed cell death in bacterial populations. Science. 267:836-7.

Abubakar, I., L. Irvine, C. F. Aldus, G. M. Wyatt, R. Fordham, S. Schelenz, L. Shepstone, A. Howe, M. Peck, and P. R. Hunter. 2007, pp. 33-41. A systematic review of the clinical, public health and cost-effectiveness of rapid diagnostic tests for the detection and identification of bacterial intestinal pathogens in faeces and food. Health Technol Assess. 11:1-216.

Garland, S., J. Wood, and L. F. Skerratt. 2011. Comparison of sensitivity between real-time detection of a TaqMan assay for Batrachochytrium dendrobatidis and conventional detection. Dis Aquat Organ. 94:101-5.

ISO. 2003. ISO 6579:2002. In, Microbiology of food and animal feeding stuffs. Horizontal method for the detection of *Salmonella* spp.

Malorny, B., D. Mäde, and C. Löfström. 2013. Real-time PCR Detection of Food-borne Pathogenic *Salmonella* spp. p. 57-77. In D. Rodríguez-Lázaro (ed.), Real-Time PCR in Food Science: Current Technology and Applications Caister Academic Press.

* cited by examiner

GENETIC ARRAY FOR SIMULTANEOUS DETECTION OF MULTIPLE *SALMONELLA* SEROVARS

RELATED APPLICATIONS

This application claims priority to U.S. provisional application 62/680,351 filed on Jun. 4, 2018, the contents of which are herein incorporated by reference in its entirety.

STATEMENT REGARDING FEDERALLY SPONSORED RESEARCH OR DEVELOPMENT

This invention was made with government support under grant award number 2012-38821-20056 awarded by the USDA/AFRI/CBG. The government has certain rights in the invention.

SEQUENCE LISTING

The instant application contains a Sequence Listing which has been filed electronically in ASCII format and is hereby incorporated by reference in its entirety. The ASCII copy, created on Jul. 19, 2019, is named 057193-000037NP_SL.txt and is 35,709 bytes in size.

FIELD OF THE INVENTION

The present invention relates to the molecular detection of frequently encountered food-borne and water borne pathogens. More particularly, the present invention relates to methods, kits, and assays for the rapid and accurate detection of *Salmonella* serovars of particular public health interest that may be carried in food or water supplies using novel primers for use in PCR and other genetic screening methodologies.

BACKGROUND OF THE INVENTION

*Salmonella* infection causes significant health and economic burden worldwide. The pathogen is one of the most important microorganisms that cause approximately 93.8 million illnesses and almost 155,000 deaths each year worldwide (44). More than 95% of all non-typhoidal *Salmonella* infections are related to food sources. It is associated with different types of food but mostly with the consumption of undercooked beef, poultry and eggs (17). Within the last decade there has been an increase in the number of food products related outbreaks linked with *Salmonella*. (59) Acute cases of gastroenteritis, resulting from pathogen infections, affect millions of persons per year in the U.S., and an estimated 22% to 30% of these cases are thought to be caused by food-borne disease or pathogens. For example, it has been reported that globally 1.3 billion cases of *salmonellosis*, occur annually, resulting in approximately 3 million deaths. While most otherwise healthy adults recover from such food poisoning within a few days of exposure, the symptoms can be at least temporarily debilitating. Because of the debilitating potential of acute *salmonellosis*, bioterrorism through deliberate adulteration of a food supply using common, or, alternatively, more rare and deadly, pathogens poses a significant potential threat to national security. Organisms listed in the national notifiable disease surveillance system and/or food-borne disease active surveillance system that have potential for use in bioterrorism include, for example, *Salmonella enterica* ssp. *enterica* (including serovars).

The traditional methods used to detect *Salmonella* in food, which rely on laborious bacteriological and serological identification, take four to seven days to complete (31). These include two-step enrichment and also selective cultural techniques that confirm *Salmonella*. Rapid and accurate detection of *Salmonella* continues to be of considerable interest for both food safety surveillance and clinical diagnosis. Among the many rapid methodologies being developed for the detection of *Salmonella* and other foodborne pathogens, the polymerase chain reaction (PCR) has been frequently applied over the past decade because of its being rapid as well as its high specificity and sensitivity (1). Detection specificity depends on the unique target sequences to the specific serovars, and primers and probes designed for the targets (10). The targets generally utilized for *Salmonella* species level identification are usually from virulence gene invA (*Salmonella* invasion protein gene) (20, 46) fimA (major fimbrial subunit encoding gene) (16) (spy (virulence gene) (39) stn (enterotoxin gene) (15) fliC (flagellin gene) (60) and hila (invasion gene transcriptional activator) (27). Regarding specific *Salmonella* serovars, it is important to find a unique target so that it will be detected only in one serovar and does not give false-positive results with other *Salmonella* serovars as well as non-*Salmonella* organisms.

Target sequences for detection can be designed from virulence genes or from hypothetical or putative proteins. It is also crucial to confirm these sequences by performing both exclusivity and inclusivity tests. These tests need to be performed before the use of rapid molecular detection systems as standard diagnostic tools for detection of *Salmonella* contamination (10). Computational genomics is used more efficiently for data mining to detect unique protein sequences of specific organisms (10). It has been observed that numerous studies have mined novel targets for pathogen detection using comparative genomic tools (33, 34, 43, 55).

*Salmonella* serovars causing human illnesses vary from outbreak to outbreak and from region to region, making predications of outbreak associated serovars practically impossible. It has been documented in the literature regarding food borne outbreaks that some serotypes are related to specific kind of foods or exposures (4, 35, 49). More than 80% of outbreaks linked to eggs and poultry are due to *S. heidelberg, s. enteritidis* and *S. hadar* contamination (32). *S. Enteritidis* is the most common cause of *Salmonella* associated foodborne illness in the United States, and *Heidelberg* is the second or third most prevalent *Salmonella* serotype found in human infections in Canada and the United States (7, 13). In Switzerland, *Salmonella* Hadar is among the top ten serovars that were reported in human infections (9). According to Morbidity and Mortality Weekly Report (8), 363 people were infected by the biggest live poultry associated outbreak with multiple *Salmonella* serovars and *S. hadar* was one of them. *Salmonella* Dublin is known as a host-adapted pathogen of cattle (61, 66). It can cause illness mainly characterized by diarrhea, pneumonia, which can cause death of adult cattle and calves (25, 62) as well as abortion and decreased milk yield in cows (14, 53). *S. dublin* can be life-threatening to individuals who are susceptible (50). Human *Salmonella* Dublin infection has been reported in the U.S. associated with consumption of certified raw milk (14). Serious disease conditions with this serovar is usually associated with risk factors such as age and debilitating disorders (36, 61). *S. kentucky* is widely present in both cattle and chicken (21), and is an emerging, drug resistant bacterium (40).

Therefore, there needs to be a rapid screening technique to simultaneously detect and identify multiple food safety threat agents. Preferably, such tools should be capable of at least detecting multiple serovars of *Salmonella* having the potential for pubic outbreaks. Further, such tools should be able to provide reliable detection techniques to identify these high frequency pathogenic agents in human food supply systems, before the *Salmonella* serovars pathogens reach the consumer.

Presently, there are no commercially mechanisms for wide and accurate screening and/or monitoring of the food supply or water supply for multiple *Salmonella* serovars. No single molecular diagnostic test suitable for use in diverse food and water matrices is available to detect multiple serovars at once. Any viable mechanism would need not only to identify the presence of a potential agent with a high degree of sensitivity and accuracy, but also need to be able to identify exactly what *Salmonella* serovars are present. Preferably, any mechanism should be capable of identifying *Salmonella* serovars S. heidelerg, s. dublin, s. hadar, s. kentucky and S. enteritidis from closely related variants for the purpose of classifying and tracing the origin of contamination. The genomes of different strains of these serovars are not well characterized making it hard to develop molecular detection tools. Thus, the most common *Salmonella* serovars are not presently easily detected and identified.

Additionally, any screening and monitoring mechanism must be simple to operate, and preferably should be able to detect and identify multiple target serovars simultaneously. While research has considered multiplexed or simultaneous PCR-based molecular detection assays for food screening, there has not been widespread successful adaptation of PCR technologies to water and food screening. One of the known challenges in multiplexed or simultaneous PCR-based molecular detections is the need for optimization of the reactions conditions such as annealing temperatures optimal for all primer sets, avoiding primer dimers, generation of compatible amplicon sizes, and adjustment for different amplification efficiencies. Simply adjusting the PCR for detecting one agent will oftentimes make it incompatible for simultaneous detection of another agent. This is especially complicated when the sample tested for contamination is a food product.

In particular, food matrices provide a critical challenge in amplification-based pathogen detection approaches. Because of potential spoilage, pre-analytical sample processing techniques are needed to reduce the time needed to arrive at diagnosis and decision-making. Further, certain genetically-based detection mechanisms will not discriminate between live and dead organisms, with sterilized products containing non-viable bacteria or their DNA yield positive results on screening tests. Previous attempts have been made to develop multiplexed PCR assays that can simultaneously detect multiple food-borne pathogens. None of those attempts were able to produce an assay that can detect and identify the *Salmonella* serovars, and none identified highly specific targets that are unique and do not cross-react with other *Salmonella* serovars and non-*Salmonella* organisms, both in the in-vitro and in-silico validations. Highly specific primer sequences are not available for all serovars of interest, which primers are highly specific while also being suitable for simultaneous or multiplex detection of those serovars.

Thus, there remains a need in the art for methods, kits, and assays for the simultaneous, rapid and accurate detection and identification of multiple *Salmonella* serovars that may be present in food and water.

SUMMARY OF THE INVENTION

In view of the above needs, it is an object of one or more embodiments of the present invention to identify primers that may be used to identify certain *Salmonella* serovars that may be present in food and water sources.

Furthermore, it is an object of one or more embodiments of the present invention to provide methods for molecularly detecting certain *Salmonella* serovars in water and food.

Additionally, it is an object of one or more embodiments of the present invention to provide simultaneous detection and identification of multiple *Salmonella* serovars that may be present in a sample, such as a food product sample, such as through molecular detection via PCR or PCR-microplate array tests.

The various embodiments of the present invention achieve these and other objects via the discovery of novel primers for use in the molecular detection of *Salmonella* serovars, where the primers may be used in combination for the rapid, high-throughput screening PCR-based techniques to simultaneously detect multiple food safety biothreat agents. The multiplex-detection methods performed in embodiments of the present invention have improved sensitivity and specificity for the detection of multiple high-impact food-borne pathogens simultaneously. Primers are provided herein that detect with high specificity and sensitivity certain bacterial agents that pose potential catastrophic public health and economic consequences, and thus those primers may be used reliable detection techniques as described herein to identify high-impact pathogenic agents in human food supply systems before the agents reach the consumer. Various embodiments of the present invention utilize amplifiable PCR product sizes, allowing the methods to also be useful in the identification of agents and their closely related variants for the purpose of classifying and tracing the origin of contamination.

The multiple serovars for which primers have been identified in embodiments of the present invention include five particular bio-threat relevant serovars involved in high frequency in outbreaks of *Salmonella*, specifically S. heidelberg, s. dublin, s. hadar, s. kentucky and S. enteritidis. The sensitivity and specificity of the diagnostic tool were also tested in naturally and artificially contaminated milk and chicken meat.

Applicants have also identified PCR conditions that are suitable for the amplification from the five serovars under the same reaction conditions, thus making the primers identified suitable for combined use under those reaction conditions in multiple simultaneous PCR to detect and identify those food threat agent serovars.

The novel primers described herein were developed through extensive genomic data mining and multiple layer validation of the organism serovars, by which the Applicants identified new target sequences that are believed to provide the detection methods and platforms herein with improved specificity. Moreover, many targets that were previously thought to be unique to certain serovars cross-reacted with closely related serovars. Only after thorough development, searching, screening with bioinformatics tools, have the Applicants identified unique targets for the five *Salmonella* serovars.

Sensitivity assays performed also confirmed usefulness of the primers for detection of small amounts of target DNA. As such, Applicants invention comprises a suitable platform to simultaneously detect small amounts of foodborne pathogen and threat agents specifically and in real-time.

Thus, for the first time Applicants have identified primers for major *Salmonella* serovars that may be readily combined into common assays for the rapid and accurate detection of primary food threats. Moreover, these unique primers and methods utilizing the primers allow isolation of these five serovars directly from the enrichment step. The primers are identified fully below.

The various primers may be used alone to detect and identify a selected serovar, or may be used in combination and/or tandem to detect and identify whether any of a plurality of Salmonella serovars are present in a sample. When used in tandem or combination, one embodiment of the invention comprises using primer pairs designed for detecting two or more different Salmonella serovars in a common PCR-microplate array or, alternatively, in a one-tube multiplex PCR. In such embodiments, the various different primer pairs are selected such that all utilized pairs can operate under the same conditions (e.g., melting temperatures) such that the PCR process can be run simultaneously on the macroarray or one-tube array. Most preferably, the macroarrays and/or multiplex one-tube arrays contain primer pairs sufficient to detect and identify one or more Salmonella serovars simultaneously. Further, particularly with respect to multiplex one-tube PCR, such embodiments can optionally use different probes specific to the target gene containing different dyes of different emission capacity to assist in multiplex detection.

One particular preferred embodiment of the invention comprises customized PCR-microplate arrays of 96, 48 or 63 wells useful for the rapid identification of *S. heidelberg, s. dublin, s. hadar, s. kentucky* and *S. enteritidis*. These PCR-microplate arrays contain suitable primers for the pathogens such that the same PCR conditions may be used to run all the samples of the three different plates for analysis under real-time PCR. Thus, these PCR-microplate arrays constitute a rapid (e.g., less than 1 hr overall testing time), high-throughput screening PCR-macro-array technique to simultaneously detect multiple *Salmonella* serovars that pose food safety threats.

Additional embodiments of the invention include hand-held devices for point-of-use detection using SPR and impedimetric biosensor technologies. Such hand-held devices would be suitable, for example, in use for the detection of common food-borne pathogens at industrial and small scale farming levels.

The various embodiments of the invention having thus been generally described, several illustrative embodiments will hereafter be discussed with particular reference to several attached drawings and in view of various experimental examples.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Experiments

The various experiments described herein illustrate the novel plasmid target-based PCR assays and testing methodology utilizing the same for the detection of *Salmonella* serovars. These experiments also provide support for the effectiveness of the unique targets for identifying *Salmonella* serovars *heidelberg, hadar, enteritidis, kentucky* and *dublin* which are important from a public health and economic perspective. Further, these experiments demonstrate improved assays for detecting multiple *Salmonella* serovars, which include delivery of results in a shorter amount of time.

Materials

A total of one hundred and sixteen (116) *Salmonella* serovars, and thirty-five (35) non-*Salmonella* serovars were used for in-vitro validation of the present invention. The *Salmonella* serovars and strains were obtained from different sources: American Type Culture Collection (ATCC) (Manassas, Va.); United States Department of Agriculture (USDA) diagnostic Lab (Athens, Ga.); Auburn University College of Veterinary Medicine (Auburn, Ala.); Department of Poultry Science, Auburn University; Department of Biological Sciences, Auburn University and National Veterinary Service laboratories (NVSL) (Ames, Iowa). Prior to use all the *Salmonella* serovars were confirmed by culture on Xylose Lysine Tergitol₄ agar (XLT4) *Salmonella* selective media and analyzed for the presence of the invasive invA gene (specific to *Salmonella*) following the procedure performed by Woubit et al. 2012 (62).

Figure 1:
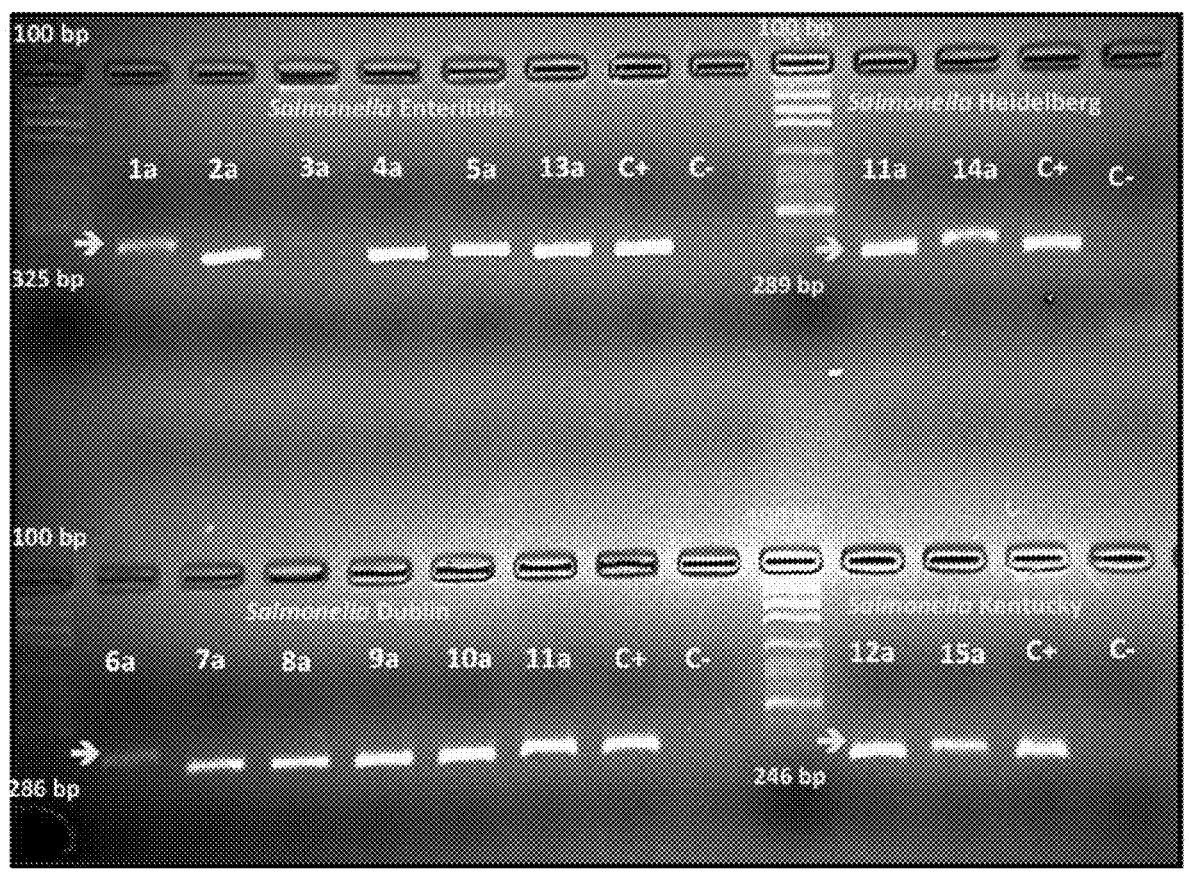
FIG. 1 illustrates various gels obtained from PCR under equivalent conditions for amplification of multiple strains of *Salmonella* serovars; *Enteritidis* strains, *Heidelberg* strains, *Kentucky* strains and control positive strains for each serovar and further illustrate validation of those primers as having a very specific detection profile.
Figure 2:
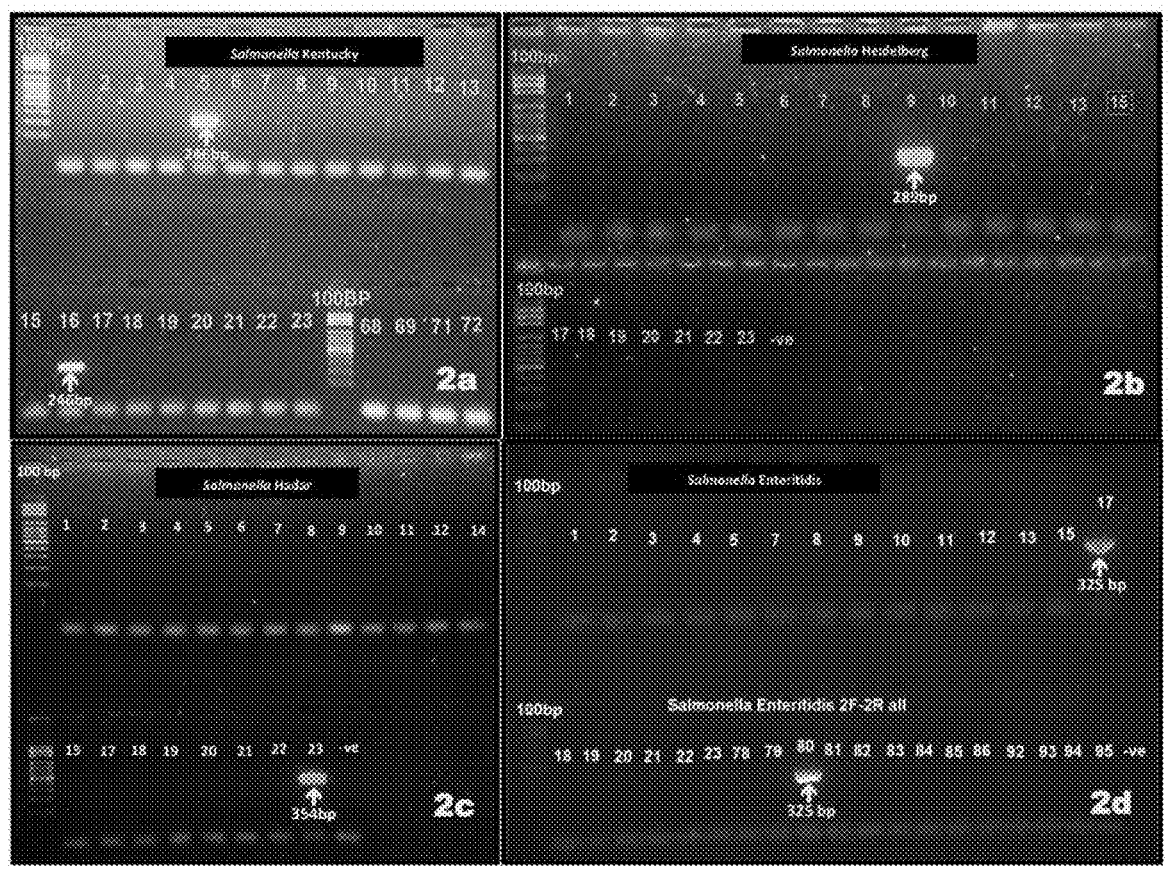
FIG. 2 illustrates the unique amplification of target serovars in the validation of serovar specific primers, including: panel 2a, serovar *Kentucky* specific amplifications of *S. kentucky* C3 11-12-1 and *S. kentucky* 8195 in lanes 5 and 16; panel 2b, serovar *Heidelberg* specific amplification of *S. heidelberg* b 11-21-13 in lane 9; panel 2c, serovar Hadar specific amplification of *S. hadar* 11025; panel 2d serovar *Enteritidis* specific primers providing target amplification *S. enteritidis* (ATCC® 13076TM) on lane 80 and cross reaction with *Salmonella* O:gim:—11663-31 in lane 17.

Various bacterial strains used in the experiments to establish exclusivity of the PCR detection are listed in Table 1 below. The 35 pure cultures of non-*Salmonella* strains listed in Table 1 were used for exclusivity test after further verification for *Salmonella* invA gene amplification. All the non-*Salmonella* strains yielded negative PCR results when tested using with any of the five primers specific for *S. heidelberg, s. enteritidis, s. hadar, s. kentucky* and *S. dublin*, as illustrated in FIG. 2.

TABLE 1

Non Salmonella organisms used for the assay validation

| Serial No. | Lab ID. | Non salmonella strains | Id/strain number | Salmonella Specific invA PCR |
|---|---|---|---|---|
| 1 | 28 | Bacillus cereus | 14579 | — |
| 2 | 9 | Campylobacter jejuni | 29428 | — |
| 3 | 25 | Campylobacter coli | 43478 | — |
| 4 | 21 | Campylobacter jejuni | 33291 | — |
| 5 | 32 | Clostridium perfringens | 8432 | — |
| 6 | 33 | Clostridium perfringens | 43402 | — |
| 7 | 34 | Clostridium perfringens | 3631 | — |
| 8 | 35 | Clostridium perfringens | 9865 | — |
| 9 | 1 | E. coli O145 | 2.3636 | — |
| 10 | 2 | E. coli O157 | 6.1593 | — |
| 11 | 3 | E. coli O111 | 0.2056 | — |
| 12 | 4 | E. coli O121 | 5.0959 | — |
| 13 | 5 | E. coli O103 | 90.1219 | — |
| 14 | 6 | E. coli O104 | 11.1587 | — |
| 15 | 7 | E. coli O26 | 99.0704 | — |
| 16 | 8 | E. coli O45 | 11.1079 | — |
| 17 | 12 | Listeria monocytogenes | Auburn USDA lab | — |
| 18 | 13 | Listeria monocytogenes | 13932 | — |
| 19 | 16 | Listeria monocytogenes | 35 | — |
| 20 | 19 | Listeria monocytogenes | 51 | — |
| 21 | 20 | Listeria monocytogenes | 33 | — |
| 22 | 22 | Listeria monocytogenes | 38 | — |
| 23 | 24 | Listeria monocytogenes | 13912 | — |
| 24 | 27 | Listeria monocytogenes | 18 | — |
| 25 | 14 | Pseudomonas aerogenes | NR-15 | — |
| 26 | 10 | Shigella dysenteriae | ATCC 11456A | — |
| 27 | 18 | Shigella sonnei | NA | — |
| 28 | 29 | Staphylococcus aureus | 12600 | — |
| 29 | 30 | Staphylococcus aureus | 13565 | — |
| 30 | 31 | Staphylococcus aureus | 27664 | — |
| 31 | 11 | Yersinia | ATCC 11960 | — |
| 32 | 15 | Yersinia pestis | NA | — |
| 33 | 17 | Yersinia pestis | NR -624 | — |
| 34 | 23 | Yersinia enterocolitica | ATCC 700823 | — |
| 35 | 26 | Yersinia | ATCC908 | — |

TABLE 2

Specificity and Sensitivity Testing of the Designed Primers by both Conventional and Real Time PCR

| ID | Salmonella enterica serovars | invA gene | Heidelberg | Hadar | Kentucky | Enteritidis | Dublin |
|---|---|---|---|---|---|---|---|
| 1 | Salmonella Montevideo o-group C1 | + | − | − | − | − | − |
| 2 | Salmonella Senftenberg E4 11-21-13 | + | − | − | − | − | − |
| 3 | Salmonella Kiambu ATCC MC 319 TX B | + | − | − | − | − | − |
| 4 | Salmonella Javiana Ps 11-21-13 | + | − | − | − | − | − |
| 5 | Salmonella Kentucky C3 11-12-13 | + | − | − | + | − | − |
| 6 | Salmonella Enteritidis D1 11-21-13 | + | − | − | − | + | − |
| 7 | Salmonella Muenchen C 2 11-21-13 | + | − | − | − | − | − |
| 8 | Salmonella Typhimurium B 11-21-13 | + | − | − | − | − | − |
| 9 | Salmonella Heidelberg b 11-21-13 | + | + | − | − | − | − |
| 10 | Salmonella Mbandaka C1 11-21-13 | + | − | − | − | − | − |
| 11 | Salmonella Weltevreden E 1 11-21-13 | + | − | − | − | − | − |
| 12 | Salmonella Pensacola 11272 11-21-13 | + | − | − | − | − | − |
| 13 | Salmonella Worthington 9409 11-21-13 | + | − | − | − | − | − |
| 14 | Salmonella Heidelberg 4124 11-21-13 | + | + | − | − | − | − |
| 15 | Salmonella Newport 9152 | + | − | − | − | − | − |
| 16 | Salmonella Kentucky 8195 | + | − | − | + | − | − |
| 17 | Salmonella O:gim:-11663-31 | + | − | − | − | + | − |
| 18 | Salmonella Ohio 8068-11 | + | − | − | − | − | − |
| 19 | Salmonella Braenderup 8895 | + | − | − | − | − | − |
| 20 | Salmonella Uganda 12269 | + | − | − | − | − | − |
| 21 | Salmonella 4, 5, 12:I:-10470 | + | − | − | − | − | − |
| 22 | Salmonella 6, 7:k:-7642-31 | + | − | − | − | − | − |
| 23 | Salmonella Hadar 11025 | + | − | + | − | − | − |
| 24 | Salmonella Paratyphi B-VAN-2 TARTNATE 12634 T | + | − | − | − | − | − |
| 25 | Salmonella Thompson 7642-13 A | + | − | − | − | − | − |
| 26 | Salmonella Typhimurium | + | − | − | − | − | − |
| 27 | Salmonella Infantis | + | − | − | − | − | − |
| 28 | Salmonella Reading | + | − | − | − | − | − |
| 29 | Salmonella Typhimurium SN en | + | − | − | − | − | − |
| 30 | Salmonella Infantis | + | − | − | − | − | − |
| 31 | Salmonella Typhimurium SN en | + | − | − | − | − | − |
| 32 | Salmonella Paratyphi A ATCC 11511 | + | − | − | − | − | − |
| 33 | Salmonella Typhimurium | + | − | − | − | − | − |
| 34 | Salmonella Typhimurium ATCC BAA 1836 | + | − | − | − | − | − |
| 35 | Salmonella Typhimurium ATCC 700730 | + | − | − | − | − | − |
| 36 | Salmonella Typhi os ATCC 6539 | + | − | − | − | − | − |
| 37 | Salmonella Schwarzengrund 12-1 | + | − | − | − | − | − |
| 38 | Salmonella Schwarzengrund 11-1 | + | − | − | − | − | − |
| 39 | Salmonella Schwarzengrund 11-2b R | + | − | − | − | − | − |
| 40 | Salmonella Schwarzengrund 11-3 | + | − | − | − | − | − |

TABLE 2-continued

Specificity and Sensitivity Testing of the Designed Primers by both Conventional and Real Time PCR

| ID | Salmonella enterica serovars | invA gene | Heidelberg | Hadar | Kentucky | Enteritidis | Dublin |
|---|---|---|---|---|---|---|---|
| 41 | Salmonella Schwarzengrund 37-1 | + | − | − | − | − | − |
| 42 | Salmonella Enteritidis 35-1 | + | − | − | − | + | − |
| 43 | Salmonella Enteritidis 35-2 | + | − | − | − | + | − |
| 44 | Salmonella Enteritidis 35-3 | + | − | − | − | + | − |
| 45 | Salmonella Schwarzengrund 37-3 | + | − | − | − | − | − |
| 46 | Salmonella Schwarzengrund 11-2a Y | + | − | − | − | − | − |
| 47 | Salmonella Schwarzengrund 12-2 | + | − | − | − | − | − |
| 48 | Salmonella Enteritidis 35 | + | − | − | − | + | − |
| 49 | Salmonella Schwarzengrund 12 | + | − | − | − | − | − |
| 50 | Salmonella Enteritidis 35-4 | + | − | − | − | + | − |
| 51 | Salmonella Typhimurium 56 | + | − | − | − | − | − |
| 52 | Salmonella Typhimurium 3 | + | − | − | − | − | − |
| 53 | Salmonella Enteritidis 35-5 | + | − | − | − | + | − |
| 54 | Salmonella Schwarzengrund 37 | + | − | − | − | − | − |
| 55 | Salmonella Typhimurium 56-2 | + | − | − | − | − | − |
| 56 | Salmonella Typhimurium 56-3 | + | − | − | − | − | − |
| 57 | Salmonella Saintpaul 7-14-11 ATCC 9712 | + | − | − | − | − | − |
| 58 | Salmonella Adelaide | + | − | − | − | − | − |
| 59 | Salmonella Reading | + | − | − | − | − | − |
| 60 | Salmonella arizonae | + | − | − | − | − | − |
| 61 | Salmonella Senftenberg | + | − | − | − | − | − |
| 62 | Salmonella Rubislaw | + | − | − | − | − | − |
| 63 | Salmonella Anatum | + | − | − | − | − | − |
| 64 | Salmonella Newport | + | − | − | − | − | − |
| 65 | Salmonella Mbandaka | + | − | − | − | − | − |
| 66 | Salmonella Oranienburg | + | − | − | − | − | − |
| 67 | Salmonella Liverpool | + | − | − | − | − | − |
| 68 | Salmonella Muenster | + | − | − | − | − | − |
| 69 | Salmonella Litchfield | + | − | − | − | − | − |
| 70 | Salmonella 6 7:k:- | + | − | − | − | − | − |
| 71 | Salmonella Rough o:gim:- | + | − | − | − | − | − |
| 72 | Salmonella Inverness | + | − | − | − | − | − |
| 73 | Salmonella Dublin M06-53175-Dr Ogi | + | − | − | − | − | + |
| 74 | Salmonella Dublin M07-17378-Dr Ogi | + | − | − | − | − | + |
| 75 | Salmonella Tennessee (ATCC® 10722TM) | + | − | − | − | − | − |
| 76 | Salmonella Agona (ATCC® 51957TM) | + | − | − | − | − | − |
| 77 | Salmonella Paratyphi C (ATCC® 13428TM) | + | − | − | − | + | − |
| 78 | Salmonella Bareilly (ATCC® 9115TM) | + | − | − | − | − | − |
| 79 | Salmonella Pullorum (ATCC® 13036TM) | + | − | − | − | − | − |
| 80 | Salmonella Enteritidis (ATCC® 13076TM) | + | − | − | − | + | − |
| 81 | Salmonella Newport (ATCC-6962) | + | − | − | − | − | − |
| 82 | Salmonella Paratyphi B (ATCC 8759) | + | − | − | − | − | − |
| 83 | Salmonella Javiana (ATCC-BAA-1593) | + | − | − | − | − | − |
| 84 | Salmonella arizonae (ATCC-13314) | + | − | − | − | − | − |
| 85 | Salmonella Muenchen (ATCC-BAA-1674) | + | − | − | − | − | − |
| 86 | Salmonella diarizonae (ATCC-12325) | + | − | − | − | − | − |
| 87 | Salmonella Thompson (ATCC-8391) | + | − | − | − | − | − |
| 88 | Salmonella Choleraesuis (ATCC-55105) | + | − | − | − | − | − |
| 89 | Salmonella Infantis (ATCC 51741) | + | − | − | − | − | − |
| 90 | Salmonella Cerro (ATCC 10723) | + | − | − | − | − | − |
| 91 | Salmonella Gaminara (ATCC 8324) | + | − | − | − | − | − |
| 92 | Salmonella Johannesburg (14-5818) | + | − | − | − | − | − |
| 93 | Salmonella Wandsworth (11-7160) | + | − | − | − | − | − |
| 94 | Salmonella 4-5-12i (14-5821) | + | − | − | − | − | − |
| 95 | Salmonella Subsp. arizonae 48:g, Z51:_(13-1516) | + | − | − | − | − | − |
| 96 | Salmonella Baildon (14-4442) | + | − | − | − | − | − |
| 97 | Salmonella Choleraesuis (14-3829) | + | − | − | − | − | − |
| 98 | Salmonella Infantis (14-4189) | + | − | − | − | − | − |
| 99 | Salmonella Newport (14-2911) | + | − | − | − | − | − |
| 100 | Salmonella Schwarzengrund (13-5829) | + | − | − | − | − | − |

TABLE 2-continued

Specificity and Sensitivity Testing of the Designed Primers by both Conventional and Real Time PCR

| ID | Salmonella enterica serovars | invA gene | Heidelberg | Hadar | Kentucky | Enteritidis | Dublin |
|---|---|---|---|---|---|---|---|
| 101 | Salmonella Enteritidis 145352 | + | − | − | − | + | − |
| 1a | Salmonella Enteritidis 12D14456 | + | − | − | − | + | − |
| 2a | Salmonella Enteritidis 775 | + | − | − | − | + | − |
| 3a | Salmonella Enteritidis 420 | + | − | − | − | −[1] | − |
| 4a | Salmonella Enteritidis 1614 | + | − | − | − | + | − |
| 5a | Salmonella Enteritidis 2640 | + | − | − | − | + | − |
| 13a | Salmonella Enteritidis | + | − | − | − | + | − |
| 6a | Salmonella Dublin 598 | + | − | − | − | − | + |
| 7a | Salmonella Dublin 941 | + | − | − | − | − | + |
| 8a | Salmonella Dublin 1225 | + | − | − | − | − | + |
| 9a | Salmonella Dublin 1958 | + | − | − | − | − | + |
| 10a | Salmonella Dublin 1618 | + | − | − | − | − | + |
| 11a | Salmonella Heidelberg | + | − | − | − | − | − |
| 14a | Salmonella Heidelberg | + | + | − | − | − | − |
| 12a | Salmonella Kentucky | + | + | − | − | − | − |
| 15a | Salmonella Kentucky | + | − | − | + | − | − |

[1]A very weak amplification of similar size observed.

The suitability of the various serovar/strain specific primers designed by Applicants for both highly selective and highly sensitive use was confirmed, as described in the various examples and experiments below. Other preferred primers, and preferred uses of the primers in combination with other primers, are identified in the various examples that follow.

Genomic DNA from all *Salmonella* serovars and non-*Salmonella* organisms, unless otherwise noted herein, was extracted according to the manufacturer's procedure used in bacterial DNA extraction (QiaAmp® DNA Mini Kit (Qiagen™, Valencia, Calif.). All organisms were cultured in Tryptic Soy Broth and incubated for 18 h at 37° C. before DNA extraction. All artificially and naturally contaminated food samples were pre-enriched in non-selective Buffered Peptone Water (BPW) followed by selective enrichment in Rappaport-Vassiliadis *Salmonella* Enrichment Broth (RVS). For DNA extraction, 1 ml of selective enrichment culture from artificial and natural inoculation were collected in 1.5 ml tube and centrifuged at 5000 g for 10 minutes at +4° C. The supernatant was carefully discarded without disrupting the pellet; the pellet was then used for DNA xtraction using DNeasy® Blood and Tissue kit following the manufacturer's instructions (Qiagen™, Valencia, Calif.). The quality of DNA was assayed both by using NANODROP 2000C spectrophotometers (Thermo Fisher Scientific®, Carlsbad, Calif.) and by agarose gel electrophoresis. Extracted DNA was stored at −20° C.

Unless otherwise indicated herein in the various specific laboratory examples, all PCR reactions were set up in an isolated PCR station (AirClean® Systems, NC) that was ultraviolet (UV)-sanitized daily and after each use.

As noted above, primers are not available which are highly sensitive and specific while still being suitable for use in a simultaneous multi-serovar array. As such, Applicants designed various primers as disclosed herein that would be suitable for use in simultaneous detection systems. To this end, Applicants used text mining, genomic data mining, sequence analysis and comparison tools to design the various primers listed in Table 3 below. Indeed, the primers for some serovars of *S. enteritidis* were designed from a target gene reported to be unique for this serovar because of obstacles of finding unique targets from genome mining and some of the targets obtained cross-reacted in vitro with other *Salmonella* serovars. All primers were independently designed based upon direct genomic information without earlier reference to other known primers.

During the process of selection and design, the primers were initially validated for unique site recognition and strength of binding by using genomic DNA template of the respective organism. For each of the organisms selected, Applicants obtained genome sequences for the organisms and a BLAST (Basic Local Alignment Search Tool) search was used in selecting target regions. During design, Applicants also analyzed oligo-dimer and hair-loop characteristics of potential primer sequences in an effort to standardize primers to have similar melting temperatures, a prerequisite for simultaneous PCR usage. All of the *Salmonella* serovars and strains used in the development of the primers and tests were positive for the invA gene specific for the genus *Salmonella*. Most of the virulent *Salmonella* serotypes have the invA gene, which is responsible for invasion of epithelia cells and for pathogenicity (52).

Completed and incomplete (contigs) genome sequence data for the five selected *Salmonella* serovars; other serovars and non-*Salmonella* organisms were retrieved to VECTOR NTI 11 database (Thermo Fisher Scientific®, Carlsbad, Calif.) from National Center for Biotechnology Information (NCBI) microbial genome-sequencing database. To identify specific unique target sequences for each of the five selected *Salmonella* serovars, approximately 4500 annotated protein-coding sequences (CDSs) of each of the selected strain of a serovar were screened for the similarity of nucleotide sequence against genomes from other *Salmonella* serovars and non-*Salmonella* organisms available at NCBI through the Basic Local Alignment Search Tool (BLAST) for nucleotide. The CDSs of a given serovar were selected as the potential targets for detection if it matched with those of the same serovars in the database, with lowest E 10-50 values, more than 98% query coverage and 100% identity coverage. The target CDSs sequences were then uploaded to VECTOR NTI database along with closely *Salmonella* serovar and non-*Salmonella* organisms from NCBI databases and blasted and aligned to further evaluate the uniqueness of the target amino acid sequence and its nucleotide counterpart. Similarly the targets were also tested against the *Salmonella* and non-*Salmonella* organisms found in Pathosystems Resource Integration Center (PATRIC) databases (64). When the target matched 100% to the selected serovars and did not cross-react with other *Salmonella* and non-*Salmo-* nella organisms, it was selected for primer design from its most polymorphic site. The designed primer was further blasted on 268 complete, 2395 scaffold and 4543 contig's of Salmonella serovars on both PATRIC and NCBI databases. In addition, primers were validated for non-specific binding on the genome sequences of 15 closely related species including Escherichia coli and other members of the family Enterobacteriaceae. Primers were then used to run in-silico PCR of target serovar and to verify none-target amplification with other serovars on 45 fully sequenced Salmonella. Primers were further used to analyze motif search to check inter and intra-genomic specificities, this later validation was performed using VECTOR NTI motif search engine. This allowed confirmation of single site binding within the target genome and no cross binding to other Salmonella serovars and closely related organisms. Primers that fulfilled these criteria were analyzed for their thermodynamic properties including dimer and hair-loop formation, palindromes, Tm, and 3'GC content before final ordering. Probes for multiplex TAQMAN® assay were designed for three serovars, i.e., Enteritidis, Heidelberg and Dublin using PrimerQuest™ of Integrated DNA Technologies® (IDT, Ames, Iowa). The reporter dyes for serovars Enteritidis, Heidelberg and Dublin were FAM™, ROX™ and CY5™, respectively; all the probes were modified to carry a Black Hole Quencher™ Dye (BHQ) at their 3'end. The primers and probe were ordered from Integrated DNA Technologies®.

Virtual PCR results provided an initial indication regarding the specificity of the developed primers for the serovars, and conventional PCR specific amplification from different organisms species was confirmed the in-silico findings. Specifically, primers were validated in-silico on a wide range of target and non-target organisms, including 45 fully sequenced Salmonella serovars, 268 complete, 2395 scaffold and 4543 contig's of Salmonella serovars on both PATRIC and NCBI databases. In addition, primers were validated for non-specific binding on the genome sequences of 15 closely related species including Escherichia coli and other members of the family Enterobacteriaceae.

Following this in-silico testing, those primers identified in Table 3 below were tested further using conventional PCR.

Initial validation involved testing of these primers with the genomic DNA of the corresponding Salmonella serovars. The PCR was performed in a total of 20 µl volume containing 10 µl of PWO master mix (DNA Polymerase, reaction buffer with 4 mM MgCl2 and PCR-grade dNTP's (each 0.4 mM) in a total volume of 250 µl) (SIGMA, Mannheim, Germany), 8 µl of PCR water, 1 µl of 20 µM of primer pair and 1 µl of 30 ng/µl genomic DNA. The thermal cycling program (Mastercycler® Pro, Eppendorf®, Hamburg, Germany) included: initial denaturation for 2 min at 94° C., followed by 30 cycles of 15 seconds at 94° C., 15 seconds at 60° C., and 15 seconds at 72° C. then 1 cycle of 72° C. for 5 min. Four microliters of the PCR product was mixed with 2 µl of 6× loading dye and loaded onto 1.5% agarose gel, which ran for 40 minutes at 100 volts. The PCR product was analyzed for the presence of bands after the gel was stained using GelRed® (Biotium, Hayward, Calif.), images were analyzed using AlphaView® software (AlphaView® software, San Leandro, Calif.).

In addition to conventional PCR confirmation, SYBR Green Real Time PCR assay was performed using MX3000PTM (Agilent® Technologies Inc., Santa Clara, Calif.) for further validations of primers provided a specific single band with the conventional PCR assay. The PCR was done in a 20 µl reaction volume comprising 7.7 µl of PCR grade water, 10 µl of 2× SYBR® Green master mixes (Roche™ Life Science, Indianapolis, Ind.), 0.5 µL of forward and reverse primer and 1 µl of DNA. The thermal cycling program for the real-time PCR were as follows: 95° C. for 15 min, followed by 30 cycles of denaturation at 94° C. for 30 seconds, annealing at 60° C. for 30 seconds, and extension at 72° C. for 30 seconds. The PCR results were analyzed using MxPro® software (Agilent® Technologies Inc.).

The real time PCR assays using the newly created primers were tested by five-fold serial dilutions of the genomic DNA of each of the five serovars, in order to determine the minimum concentration of DNA that can be detected. Before the assay, the initial concentration of stock DNA was measured using NANODROP 2000C spectrophotometers. DNA was serially diluted using PCR grade water to femtogram (fg) concentrations.

TABLE 3a

Sequences of primers and probes designed

| Primers and probes | Size (bp) | Sequences (5' to 3') | SEQ ID NO: | Target size (bp) | GenBank accession no. or strain (position) |
|---|---|---|---|---|---|
| Primer-probe combinations for assays | | | | | |
| Heidelerg-1R-s | 20 | GCAGTTCATTCGCTTTGTCG | 1 | 156 | NC_021810 (1677692-1677980) |
| Heidelberg-1F | 21 | CGGAAAATACGTCTCATGTCC | 2 | | |
| Heidelberg probe | 24 | ROX/TAGTCCATCACCCAGCGCAGTTTC/IABkFQ | 3 | | |
| Enteritidis-all-2R | 19 | CTGGCATCAAGAATGTCGT | 4 | 325 | U66901.1 (609-933) |
| Enteritidis-all-2F | 20 | CGCAAAAATCAGGATGGCTC | 5 | | |

TABLE 3a-continued

Sequences of primers and probes designed

| Primers and probes | Size (bp) | Sequences (5' to 3') | SEQ ID NO: | Target size (bp) | GenBank accession no. or strain (position) |
|---|---|---|---|---|---|
| Enteritidis probe | 23 | FAM/TACGGCGATTTCTACCGTGTCGT/IABkFQ | 6 | | |
| Dublin-1R-s[2] | 27 | GATTTACGACTGTTGGTGTTTAAGCTG | 7 | 118 | NC_011204 (46817-46934) |
| Dublin-1F-p[a] | 26 | GTGAGAAATCCAGATACCAGAAAGAA | 8 | | |
| Dublin probe | 23 | CY5/AGAACTACGCACGGCAATTTCGA/IABkFQ | 9 | | |
| Primer combinations for conventional and SYBR Green PCR assay validation | | | | | |
| Heidelberg-1F[a] | 21 | CGGAAAATACGTCTCATGTCC | 10 | 289 | NC_021810 (1677692-1677980) |
| Heidelberg-1R[a] | 21 | GATTCTTCACGCACAATATCC | 11 | | |
| Hadar-1F[a] | 24 | AATCTGAACTTGAGAAATCAATCC | 12 | 354 | FR686852.1 (93097-93120 |
| Hadar-1R[a] | 22 | CCGTGAGGAGATTATTTAGCCC | 13 | | |
| Kentucky-2F[a] | 21 | ACGTTGAGCGAGTTTATCGCT | 14 | 246 | EDX46695.1 |
| Kentucky-2R[a] | 20 | CAATGGTCTGTTATGGGGAA | 15 | | |
| Enteritidis-all-2R[a] | 19 | CTGGCATCAAGAATGTCGT | 16 | 325 | U66901.1 (609-933) |
| Enteritidis-all-2F[a] | 20 | CGCAAAAATCAGGATGGCTC | 17 | | |
| Dublin-1F | 26 | GTGAGAAATCCAGATACCAGAAAGAA | 18 | 286 | NC_011204 (46817-47102) |
| Dublin-1R | 23 | CGGGATGGTTTAATTATCAATGA | 19 | | |

[2]Primers used for multiplex conventional PCR assay.

TABLE 3b

Sequences of primers and probes designed with Targeted Sequence

| Primer Name | Size (bp) | Sequence (5'-3') | SEQ ID NO: | Target (bp) | Target gene | Targeted Sequence | SEQ ID NO: |
|---|---|---|---|---|---|---|---|
| Javiana-3mF | 20 | GTTGAATGGAGGAAGCGTCC | 20 | 136 | Type V secretory pathway adhesin AIDA | GTTGAATGGAGGAAGCG TCCAGGTTGAAGGTAAT TATGGCATTTTGATGCTC TATAATAATTCACAAGC CACCCTGATGGGCACCG AGGTCACCGCAACGGCG GAAACAACTAGCGGCAT AGTGTCACAGCAAGGC | 93 |
| Javiana-3R | 20 | CCTTGCTGTGACACTATGCCG | 21 | | | | |

TABLE 3b-continued

Sequences of primers and probes designed with Targeted Sequence

| Primer Name | Size (bp) | Sequence (5'-3') | SEQ ID NO: | Target (bp) | Target gene | Targeted Sequence | SEQ ID NO: |
|---|---|---|---|---|---|---|---|
| Oranienburg-SS-new-2R | 23 | CATTAGATATGAACAAGCGACCG | 22 | 188 | Hypothetical protein | CATTAGATATGAACAAGCGACCGGACTCAACCGTATTAAAGCGCATATAAATACTGCTAACAAATTCACCCACATTTATTGGCATTGGTGAATTTTTTGGTTCTTTACGCTTTCCAATTGTCTTGGCTTCAATAACTACCATTCTATTTAAAAAACCCGTCCCAGCCTCACGGCTTGAAAATGCACTC | 94 |
| Oranienburg-SS-new-2F | 21 | AGTGCATTTTCAAGCCGTGAG | 23 | | | | |
| Oranienburg-SS-new-1R | 23 | GAGTTTTACCAACTGATGTCGGG | 24 | 175 | Hypothetical Protein | AGTTTTACCAACTGATGTCCGGGGCTAAAACTGCAATATATAAATTACTCGTTAGCGTTCCCTTATATGACCATCTGCCAGAAATTAAAGAAGCCATTGACGCAACGGAAAACGCCAATGCTAATTCAGGGCAATATGTTCTAGTGTTTTCAATTTGCCAATCAAACAAGCCAGTT | 95 |
| Oranienburg-SS-new-1F | 21 | AACTGGCTTGTTTGATTGGCA | 25 | | | | |
| Paratyphi B-4R | 20 | ATGAGTCCAATCGTGCCTGC | 26 | 213 | SPAB_05693 - EcoKI restriction-modification system protein HsdS | ATGAGTCCAATCGTGCCTGCGATACTAATATATAGATCGTTTTTACTTATGGTGTAATTGCTGATAGCAGATAAGTATCGGAGTCTAAATACTTAATCGTGGAAAGATTTACGCTTCCATTTTCGAAGTCAGTAACTCTAATATATGGATGTTCTGTTGCGGTATTAAGTAAAGCTTTACCTTTGGGAAGCCTTTTTCCACCCTTTACTTCA | 96 |
| Paratyphi B-4F | 23 | TGAAGTAAAGGGTGGAAAAAGGC | 27 | | | | |
| Paratyphi A-SF | 23 | GGACTATTCAGGATGCTGTGAAG | 28 | 111 | SSPA2266 - hypothetical protein | GGACTATTCAGGATGCTGTGAAGTTTTGCAGGGAGACTGGAAGACAAGATGCTGGCTCAGCCATGGAGGCATGGAATGCCTGCCGCACCGCCATGCTCCAAGGTAGCCAAC | 97 |
| Paratyphi A-5R | 19 | GTTGGCTACCTTGGAGCAT | 29 | | | | |
| Paratyphi A-4R | 19 | TGAGGTCGCCAAGTTCTGC | 30 | 264 | SSPA2266 - hypothetical protein | GACTTGTCGATATTGATTCAGGCGCAGAGGATCATTGGAAATATTCAACTCAGTGCATAACACCTGCATCTGGAAAGACGTACCGTATTGAGTCTATTCCTCTCTACACAGTCTCGCAACCAGTACCAGTACCAGAACGCGAACGTATTCGCCGTGAACATGCTGAATGGTCTGATGCCACATTCGGCGATGTTGGCCCCATCGGTCCACTGAAGCACCTCTCA | 98 |

TABLE 3b-continued

Sequences of primers and probes designed with Targeted Sequence

| Primer Name | Size (bp) | Sequence (5'-3') | SEQ ID NO: | Target (bp) | Target gene | Targeted Sequence | SEQ ID NO: |
|---|---|---|---|---|---|---|---|
| | | | | | | AAAGAGGCATTGGAAAC TGCCGCAGAACTTGGCG ACCTCA | |
| Paratyphi A-4F | 24 | GACTTGTCGA TATTGATTCA GGCG | 31 | | | | |
| Tennes-4F | 24 | CCACAGCAGT ACATAGAAAG GACC | 32 | 198 | DNA transfer protein | CCACAGCAGTACATAGA AAGGACCGGGAGAACCG CAAACGTACTTAGAAAC CTTGACTCGGGCCTGTCC AGCGTAACCAGCACTGT CCTCAATGCTATAGCCA ACTCCACATCAGGTGCT GTTGTTGGCGGTGCAGG TGGAGGGATTGCTGGCG CTGCTGCCGGGGCGTTG GCTGGAGCGGGACTGAA AGGCATCGTT | 99 |
| Tennes-4R | 20 | AACGATGCCT TTCAGTCCCG | 33 | | | | |
| Tennes-3R | 22 | AATCTGTTTGT CTCCTGGCAC C | 34 | 100 | DNA mismatch repair protein | AATCTGTTTGTCTCCTGG CACCTATAATATCCTCTC CATTTTCCACATCTTGTT CATCTATGTTATTAATGG AGTAAACACTATCCCTC AATGATTTCGC | 100 |
| Tennes-3F | 22 | GCGAAATCAT TGAGGGATAG TG | 35 | | | | |
| Hadar-1R | 22 | CCGTGAGGAG ATTATTTAGC CC | 36 | 354 | FR6868 52.1 (93097 to 93120, integrative and conjugative element ICESe4 | AATCTGAACTTGAGAAA TCAATCCGTACAGCCTAT CTTGCCACAAATATACT AGCCTATTGGGCAATAC AAGATGGTAATGCAAAA CAAGCCCTCTATGTATCG GAGCGTTGCCTGCTATG GGTATGGCACCGTATTC ACCTTGAAAAAGTCCA CAACAATACTTCTCTGCC ATTAATATTATATGGCA AAACTATATTAATATCTC CGCAGAATACTTTTCCA AACTTCAACCCTATTTTC ACGAAAAATATCTTCTG TCGTCATACTCTGCCGAT AGCGCATTAATTAATCTT ACTATATTTGAACAAAT AGGTATACTCTCTACTAT CGGGCTAAATAATCTCC TCACGG | 101 |
| Hadar-1F | 24 | AATCTGAACT TGAGAAATCA ATCC | 37 | | | | |
| Enteritidis-all-2R | 19 | CTGGCATCAA GAATGTCGT | 38 | 225 | U66901. 1 (609 to 933) fimbrial biosynthesis protein Prot6e | CTGGCATCAAGAATGTC GTCTCGTGCTGGCCATA GGCAGCCAAACGTTCAG TTTGACCTGACAATGTAC TCAACTCCAGTACTCCTC CACTGACAGGATTCCCA TAGCTGTAGCTTTGTTTT TCAACAAAACAACGCGA ACCATGCTCAGCTGCTCC ACTTGGTTCAAACCTCGC CCTCACATTCATAAAAA CGACACGGTAGAAATCG CCGTACACGAGCTTATA | 102 |

TABLE 3b-continued

Sequences of primers and probes designed with Targeted Sequence

| Primer Name | Size (bp) | Sequence (5'-3') | SEQ ID NO: | Target (bp) | Target gene | Targeted Sequence | SEQ ID NO: |
|---|---|---|---|---|---|---|---|
| | | | | | | GATTTTTGAGATGGGGG TCACCACACTTAAATTAT TGCTATTTTGCCCTGTAC ACTGCATCCTGTCACA ACATTCCATGAGCCATC CTGATTTTTGCG | |
| Enteritidis-all-2F | 20 | CGCAAAAATC AGGATGGCTC | 39 | | | | |
| Heidelberg-1R | 21 | GATTCTTCAC GCACAATATC C | 40 | 289 | fig\|1124 936.4. peg.1672, Type II restriction enzyme, methylase subunits | CGGAAAATACGTCTCAT GTCCGCTCTTCTTTACGC AGCAAAGATGAAACCTT TAGAGGTCGCCTCGAAG ATAACAGTACCTATCAG AAACTGCGCTGGGTGAT GGACTACTGGTGTGCGC TATGGTTCTGGCCAATCG ACAAAGCGAATGAACTG CCGGATCGCGGTATGTG GCTAATGGAGATGGAGA CACTGATCGACGGTATT GTCGTCACGGAAAGAGT CACTGAAGTTGCAGAGC AGGCCACCGGCAATCTG TTTGCCGACGAGGATAT TGTGCGTGAAGAATC | 103 |
| Heidelberg-1F C | 21 | CGGAAAATAC GTCTCATGTC | 41 | | | | |
| Kentucky-2R | 20 | CAATGGTCTG TTATGGGGAA | 42 | 246 | EDX466 95.1, hypothet ical protein | CAATGGTCTGTTATGGG GAAAATCATAAATATTT TTAAAGAGTTGAGAGGC GGGATTTTATTTGGTGAA AGGAACGACTACGCTAA AATTTGGCAAGAAAAAT ACCTTTCCACATCTGGGG TTGTTTCTGAGTTTGATG ATAATGTATTTTCATCAG CATATGATTATTGGCGTT CTCTTGAAGGGCCTTGG AGAGAATTATTTGTTTGT TTTTGGAACAAAGTTAG CGATAAACTCGCTCAAC GT | 104 |
| Kentucky-2F | 21 | ACGTTGAGCG AGTTTATCGC T | 43 | | | | |
| Baildon-1F-m | 25 | CGTCAGGGAA AACTGTATTT AATCG | 44 | 266 | gb\|AFC K01000924. 11:2 454- 4682, hypothetical protein LTSEB AI_3067 | TCCCTGACGACAAAATT CAATCCATTGTACTCAG GCTATTATTCTGTGGAAA GACTGAAACACTAACAG CCACTTTTAATAAAAATT TCAAAAAATTGTACCC GTTCATTTTGCGACCGAA ATATCAAATTTTAGAAA TGACTTTACAATGTTGGG ATATTTAACAGAAAAGA CTAGTGGATGGGTTACC AAGTTTGTTGATTTTTCA ATCAACGAAATTGAGAA AAACTCAGCAGACATTA AAGGATTTCACGACGAG TTTAGG | 105 |
| Baildon-1R-m | 22 | GGATGCTAAG TGAAGTGTTG GG | 45 | | | | |

TABLE 3b-continued

Sequences of primers and probes designed with Targeted Sequence

| Primer Name | Size (bp) | Sequence (5'-3') | SEQ ID NO: | Target (bp) | Target gene | Targeted Sequence | SEQ ID NO: |
|---|---|---|---|---|---|---|---|
| Baildon-2F-m | 23 | CGACCATTGCACTGATTCATCAT | 46 | 223 | gb\|AFCK01000924.11:2454-4682, hypothetical protein LTSEB_AI_3067 | GGTGAGAATAGCAAGTCGTACTCTGATTACATTAATAAAATAAAAGAAATAACTAAAACATCTAAGTACGGATATAAAGAGAAAGTTCTAAACTATGTTAAAGTAGGATTAGATGGTCAAACATTTCAGATCGATGGTAAAAAAACTAGAAATTCAATCAGATGGAACAAATTCTTTCAAATACATTGAAATATTTCTATCCCTGTTAATATCCCTTACAAGAA | 106 |
| Baildon-2R-m | 25 | TACAAAATTAGAACGACGAGAAGCA | 47 | | | | |
| Mississipi-1F | 21 | ACCCTTTCAATGTTCCTACGC | 48 | 138 | PATRIC ID: fig\|913080.3.peg.4734, hypothetical protein | ACCCTTTCAATGTTCCTACGCTCAAAATGTGATCGTGAGCTATATTTGTCACTACATGAAGATTCCGAATTGGATGCTAATTCAATGCCAGTGCCCCTTCAGGCGCGTCCAGGAATCGGAGTGCTTCAAACTGCTGGA | 107 |
| Mississipi-1R | 20 | TCCAGCAGTTTGAAGCACTC | 49 | | | | |
| Mississipi-2R | 20 | AGCGGTTCTTCTACATTGCA | 50 | 217 | PATRIC ID: fig\|913080.3.peg.4735, hypothetical protein | AGCGGTTCTTCTACATTGCAGCTAGCCAATTTTGATTTAGCGATTGCAATGGCGACCGGAGATGTATCTATTCCCCATGCTGAGAGCCCTAACGTTCGGGCTGCAAACAGTGAAGTCCCCCTTCCACAGAAAGGGTCGAGGATAACCGGAGTGTCCTTTCGATGTTTTTTTAGCACTTGGTAAGGATACTCAAGGGGAAACATCGTAAAATAAGGAC | 108 |
| Mississipi-2F | 23 | GTCCTTATTTTACGATGTTTCCC | 51 | | | | |
| Newport-1F-m | 20 | GGAATGAACTTGCCAAGGCT | 52 | 130 | Restriction endonuclease subunit S | GTTCCAGTTGATCGCAGAGGGACATGAGTTTATCAACACGTGAAACAATTCGCAGTTGCTCCTGGATAGGGAGCTAATTCGATGACAGCCTGCTGAGCTTTTTCTGTACCAAGCCTTGGCAAGTTCATTCC | 109 |
| Newport-1R-m | 20 | ATTCCAGTTGATCGCAGAGG | 53 | | | | |
| Newport-1-Probe | 23 | ATTCGATGACAGCCTGCTGAGCT | 54 | Probe | | | |
| Newport-1R-3 | 19 | TTCCAGTTGATCGCAGAGG | 55 | 128 | PATRIC ID: fig\|877468.3.peg.920, Type I restriction-modification system, | TTCCAGTTGATCGCAGAGGGACATGAGTTTATCAACACGTGAAACAATTCGCAGTTGCTCCTGGATAGGAGCTAATTCGATGACAGCCTGCTGAGCTTTTTCTGTACCAAGCCTTGGCAAGTTCATTC | 110 |

TABLE 3b-continued

Sequences of primers and probes designed with Targeted Sequence

| Primer Name | Size (bp) | Sequence (5'-3') | SEQ ID NO: | Target (bp) | Target gene | Targeted Sequence | SEQ ID NO: |
|---|---|---|---|---|---|---|---|
| | | | | | specificity subunit S | | |
| Newport-1F-3 | 20 | GAATGAACTT GCCAAGGCTT | 56 | | | | |
| Shwazengrund-2F-m | 20 | CTCAAGACCT CCAGTGCCTC | 57 | 368 | YP_002 115706.1, hypothetical protein SeSA_A2894 | CTCAAGACCTCCAGTGC CTCGCCAATCCGCCCAA TCCATGTTCGAACCATTT TGGCAAGCTCAACGAGG AGCATCCAATCTTCCATT TCTGGAGCTTCGAGCGTT ACCCAAAGATTACCCTG CCCCTCATATACACAGG TCAGCCGTTGCGCTTCAA GATCATCAATTGATGCG TAGCACTTGCTCTGACGC TCGGTGGGAAAGAAATC TTCTGCCGAAGGCCTCAT CACTCGATGCCATTTACC ATTGTTGTCACTAATGCG ATGCCGGTCATATCCTGT GTCTGCCGCTATTCGTAT ACCACGGAGTAAATTCG TGGGAATCATTAACATT AGCGGGTGTTCCGGTGT GATACGGTCATCTGGTA A | 111 |
| Shwazengrund-2R-m | 23 | TTACCAGATG ACCGTATCAC ACC | 58 | | | | |
| Shwazengrund-1R-m | 22 | CTTTCAGTTGC TGTACGTCCC T | 59 | 381 | YP_002115706.1, hypothetical protein SeSA_A2894 | ATTACGAGCAAGTGAGA GGTCCTTACATTCGATAA CGAGAACTTGATTGCGG TCTGAGCGCCAGGCAAG AAGATCAATATCCCCCG GATCACCTGGTAGATTC CTGCGAAGAATTTCAGG AAAGCCTATGCCACGTC GAACTGTCCAGCCTATTT CACGAAGTTCTCTCTCCA AAGTTTTTTCGAATGTGT GTCCTTCCCGCGCTCCAC CTAACCAAGTGTCTCTCA TACCCTCTGTGCGAAAG AAGTCACGCTTAAATTG CCCAGTGTATGCGCCAT CGAAAACGTATTTAAGG GACAGATTCAAGAGTCC TGGTGCGATAACAATTA GTGGATCGTGACTCTCTT CAATCTGTAACAAGGGA CGTACAGCAACTGAAAG | 112 |
| Shwazengrund-1F-m | 23 | ATTACGAGCA AGTGAGAGGT CCT | 60 | | | | |
| Shwazengrund-probe-1 | 24 | GAATTTCAGG AAAGCCTATG CCAC | 61 | Probe | | | |
| Choleraesuis-2R-m | 21 | TTACGCCCTG TTACATCGGT G | 62 | 190 | antirepressor (YP_216185.1) | TCCCAACCCTCGATCAA CCTGAACTTTGCGTTATT GATGGCAAAGTCGTTAC TTCCTCACTGGCTGTTGC CGATTATTTCCATAAGCC ACATAAAGACGTACTGG CTAAGATTTCCCGCCTGG ATTGTTCTGTCGAATTTA CCGAGCGAAATTTCTCG | 113 |

TABLE 3b-continued

Sequences of primers and probes designed with Targeted Sequence

| Primer Name | Size (bp) | Sequence (5'-3') | SEQ ID NO: | Target (bp) | Target gene | Targeted Sequence | SEQ ID NO: |
|---|---|---|---|---|---|---|---|
| | | | | | | CTCAGCAAATACACCGA TGTAACAGGGCGTAA | |
| Choleraesuis-2F-m | 18 | TCCCAACCCT CGATCAAC | 63 | | | | |
| Agona-1R | 27 | CATTATCAGT AGGGAGTTTT GTCTGAG | 64 | 158 | YP_008863900.1, hypothetical protein Q786_22240 | TGATATTGCTAGGCTGTT AGTTTGTGATGCCTGGA AAGCACAGGTTAAAGGG ATACCAGCCGGTTGTTTT CTACTTGCATTTTACGAT GGTGAAGACGGTGTTGA AGAGGCTGTATTGCTTA GAGCACTTTCTCAGACA AAACTCCCTACTGATAA TG | 114 |
| Agona-1F | 24 | TGATATTGCT AGGCTGTTAG TTTG | 65 | | | | |
| Agona-2R | 25 | GTAAACTCAG ATGTTTCAGG AGAAG | 66 | 414 | YP_008863900.1, hypothetical protein Q786_22240 | TTTAGAATGTAGGGTTCT TGGAGTATTTTATAGAA CACAGAAAGGGAATATA GAATTTGGTGCTGACCTT GAGAACTTTTATGCAGC TAATAATTACACTGTATA CAAAGCCAATAGAGATG TTCTTGAATTTATAGTAA ATCAACGAGATGATGGC GGTTTAGTTGGTCAGGA CTCTGAATTTAAAATTGG TAGTGTAAGATATTCATC TAGCCGTAGACATCAAT CTCAAGAGGAAAATGTT AATGTATGGGTAAATCC TAAAGATTTTTTAGGAA AAAGGTCTGCTATGTTTG GGATGACCCGTACTGGT AAGTCGAATACTGTAAA GAAAGTGATAGAAGCAA CAGAGGAAATTTCAAGA AAAGCTTTAATACTATTG GATTCAGCTTCTCCTGAA ACATCTGAGTTTAC | 115 |
| Agona-2F | 25 | TTTAGAATGT AGGGTTCTTG GAGTA | 67 | | | | |
| Arizoniae-1R-m | 21 | TCATTTGGCA CTTCAACACG G | 68 | 249 | PATRICIA: fig|41514.7.peg.3 248, Large repetitive protein SARI_03417 | TCATTTGGCACTTCAACA CGGAAGTGTGGACGCAT ATCGTTAGTTATATTGTC GTCAGCAATACCAGTGT CATTGATCAGTTCGATGC TATTAATCGCGATTTGCG TATCCACTTTCACTGTTA ATGGTGTGGACTGGCGA ATATTTCCCGCCTCATCT TCCACCGTCACTTGCAGT GTATAGCTGCCATCATCC CACGTGCTGGCAGGTGT AAATACCCAGTTACCGC CATCTTGAGTCAGTACA ATC | 116 |
| Arizoniae-1F-m | 23 | GATTGTACTG ACTCAAGATG GCG | 69 | | | | |
| Bareilly-1F-k | 23 | CCAGATCTTC GCAGGGTCAA GCT | 70 | 95 | PATRICID: fig|1196348.3.peg.3599, | CCAGATCTTCGCAGGGT CAAGCTGTGTTTGAGTG AGTTCAAAATAGCGATC AACCATTGAGCCGACAA |117 |

TABLE 3b-continued

Sequences of primers and probes designed with Targeted Sequence

| Primer Name | Size (bp) | Sequence (5'-3') | SEQ ID NO: | Target (bp) | Target gene | Targeted Sequence | SEQ ID NO: |
|---|---|---|---|---|---|---|---|
| | | | | | hypothetical protein SEEB0189_09420 | TCTTGCTTATTCCATTCCGACAGTCAC | |
| Bareilly-1R-k | 24 | GTGACTGTCGGAATGGAATAAGCA | 71 | | | | |
| Bareilly-2F-k | 24 | GGTTCTTAACGCTGTAAGCAACTC | 72 | 423 | PATRICID: fig\|1196348.3.peg.3599, hypothetical protein SEEB0189_09420 | GGTTCTTAACGCTGTAAGCAACTCAATATTAACGGATTCAAGATTTCCTTCTGCACGTAGAATCTCCAGACAAGCGGCATACAAAATTGTCTCAGAATACCTGTATTTTGATTCGCATTGCAGAGTCGCAAGCTCGGGAAGAGTGGGAACCTTTGAAGCAATAAAATCCAGACAATTTCTTAATGCCCCCCGAACCAGTTTGTCGTCACCAAATTCTAATTCAATTCTTTCCGGAAGCATGAGCACAAGTTCTGCAAAACGCACCAGACAACCCCAGTGAAGACCTCGTTCTACAATATCTCTGTTTTCATTAACGAATTCTATATTTTTGGCGTGGATCTCTCGTTGCCTTCTATCATAGCGGTTCATCTTTCGGCTATGTCTGAATCTCAAGTGCTGGTGCTTTCGCTCAGATAATTTCAT | 118 |
| Bareilly-2R | 23 | ATGAAATTATCTGAGCGAAAGCA | 73 | | | | |
| Braenderup-2F | 22 | TCACCTATCGCTGGTATAGCCT | 74 | 228 | PATRICID: fig\|930771.3.peg.3431, hypothetical protein | TCACCTATCGCTGGTATAGCCTATTATTCCACTAGAATGCATAATGCTAATAAAACACATAGATCAATCAATGTAGTATTACCACCTAAAGCTACTTACAAACAGATAATAGCTCAAGAATATTGCCCGCGCTTACAGGCTTTATTTCATTTTACACCTCCTGTCTCGTGGCAGGTTCTAAAAACTTTAGACTATCAATTTGTCGGAGAAAGAACTCCTGACCAAGCT | 119 |
| Braenderup-2R | 23 | AGCTTGGTCAGGAGTTCTTTCTC | 75 | | | | |
| Braenderup-2-Probe | 22 | GAAATAAAGCCTGTAAGCGCGG | 76 | Probe | | | |
| Braenderup-1F-m | 27 | AATTCTACAGTCAGATAGAGTTTCCCC | 77 | 349 | PATRICID: fig\|1182171.3.peg.3553, Hypothetical protein | AATTCTACAGTCAGATAGAGTTTCCCCGCCCCTTACACTTGAATCAGATATCGTGTCAGACTTTAAAGAACGATGCGAGTACTATATCGATTCCCTTAAAAAATATGACAAAGAAAACAATACCAAATAAACTTCGACTTAATGATCAAGCGAATTTCGATTATAGTTAATGGGATTACAAAATGCCTTGAAGAATTTTTGTCTGG | 120 |

TABLE 3b-continued

Sequences of primers and probes designed with Targeted Sequence

| Primer Name | Size (bp) | Sequence (5'-3') | SEQ ID NO: | Target (bp) | Target gene | Targeted Sequence | SEQ ID NO: |
|---|---|---|---|---|---|---|---|
| | | | | | | AGATATAAAATCTGCTT ACGATGTATTTAACGAT ATTTTTTCATCTAGCACT ATTAATAAACACATAAG GAGAATAACCATTCCCC TTTATGATGTCTGCAATG AAAAAAGACCTTTATTT CGAGTAAGGAAATCTGA CGCA | |
| Braenderup-1R-m | 21 | TGCGTCAGAT TTCCTTACTCG | 78 | | | | |
| Thornson-2R | 21 | ACAATTTAAC ACCCCCTACC A | 79 | 132 | PATRICID: fig\|935705. 3.peg. 4176, Putative Rhs family protein | ACAATTTAACACCCCCT ACCAAGGGATTTACCTA AAGCCTTTTGAATTTTTT TAACTTCTCTCGCTCTAT CTAAACGATTAAAGTTTT CAAATAGACTTTCTTTTA CCTTAACGGCAGATTCA AATAACCTC | 121 |
| Thornson-2F | 21 | GAGGTTATTT GAATCTGCCG T | 80 | | | | |
| Wandsworth-1R | 22 | GAAGAGTATT TGCCATTGCA AA | 81 | 288 | PATRICID-fig\|913086. 3.peg. 806, Phage tail fibers | CAATATCACAGCTAAGA ACCGTAAATAATGCATC CGAAGGGATGCGCATTC TAGTTAAGGCATATATTC AAGGGACGAATATCGGA GGTGGTGAATTCAGTTG GAACTCCACAACCACTC AAGCTGATGATGGCGGG TACATCATTAGGCCAAC TGGAATTGTTACTGGCG CCTGGATTAGAATCAGC AAAACAAGCAAGGTTTA TCTGACTGAGTATGGGG CAACCGGCGATGATACC GACGTATCAACTAAGAT ATCATCTGTTTTTGCAAT GGCAAATACTCTTC | 122 |
| Wandsworth-1F | 25 | CAATATCACA GCTAAGAACC GTAAA | 82 | | | | |
| Montevideo-2R-m-2 | 22 | GTGAATAATC CTCATCGGTT CG | 83 | 256 | PATRICID-fig\|859199. 4.peg. 4528, Hypothetical protein | GTGAATAATCCTCATCG GTTCGCAATAATTGGTAT TGATACCCTTCAAGGAC AAGCTCTCTCGCCAGTCT ATGCTGATCGGGTTGTTG TGAAGCAAAATCTCTCC CTAACACTCTATTCTGGA AATTATTAGCTCTGGTTA TTGCATTAGCATTTAGAT CATTTTCATCATTATTAA TTTCAATGAAACGAACA GGGACTTTAACTTGATA AATTCTATCTCCTAGCAC ATCCATAACGCTGCCTA AACTACTCAC | 123 |
| Montevideo-2F-m-2 | 25 | GTGAGTAGTT TAGGCAGCGT TATGG | 84 | | | | |
| Paratyphi C-1R-s | 18 | TAGCTTGGCA TTGGGTCG | 85 | | | | |

TABLE 3b-continued

Sequences of primers and probes designed with Targeted Sequence

| Primer Name | Size (bp) | Sequence (5'-3') | SEQ ID NO: | Target (bp) | Target gene | Targeted Sequence | SEQ ID NO: |
|---|---|---|---|---|---|---|---|
| Paratyphi C-1F-s | 19 | GGTTCAGGCGGAGATTGTG | 86 | 315 | PATRICID: fig\|476213.4.peg.928, hypothetical protein SPC_0871 | TAGCTTGGCATTGGGTCGTCTGTTAATCATTAAATCAGAACGTGTAAATATCTTTTCCCAAAGCTCTTTAAACTCTTTTATTTTTTCATTTTGAACAAGTCTTGGTGTCTCGGATAAAAAATCTTTAATGCCATAAATAAAATTACCAAGTTGAGCACCATCGAAGGATGAACTGGTTTTTGATTGAATGAATGTTATATCTACATCTAAATAGCTGTAATTATTAGCGATATCATCAAACGCTTCGATAGAAGTTATAATCCTTCCGTTAATGGAAATAACTAATCCATCTATAGCACAATCTCCGCCTGAACC | 124 |
| Diarizonae-1R | 23 | ACAACAGACATCACTGAGGGTGT | 87 | 101 | PATRICID: fig\|1173780.3.peg.2392, hypothetical protein | GTGGTGTCAACGGTAAAGTTCAGCGTCCGCGTCGCCGTGTTCCCTGCGATATCGGTCGCTTCCACCGTCAGCGTGTGTACACCCTCAGTGATGTCTGTTGT | 125 |
| Diarizonae-1F | 23 | GTGGTGTCAACGGTAAAGTTCAG | 88 | | | | |
| Paratyphi B-1R-s | 21 | CCTGCACTATCCTCTTCCTCC | 89 | 335 bp | SPAB_05347 - DNA topoisomerase III | GCTATTGGCCTGTCTGATCCAGAGTGTAGTTCTCTTCTTTCAGGTCTAAATACTTCGTTTGTTTCGCGTATATGGAACGACAAAAAAATCACAGCTCACCATGGCATTATCCCTACCCGAAACGCGTTTAAGTTTTCTGCGTTAAGTGAGGCAGAGCGAAGGGTATACACCCTTATCCGCCGAAATTATCTGGCACAATTTCTTCCCCTGCACGAATCTGATATTACTCGTCTGCAGTTTGACATTGGCGGGCAACTGTTCCGCACAACAGGAAGGACGGAGATTGTAATGGGCTGGAAGGTCCTTTTCAGTAAGGAGGAAGAGGATAGTGCAGG | 126 |
| Paratyphi B-1F-s | 20 | GCTATTGGCCTGTCTGATCC | 90 | | | | |
| Pullorum-1R | 20 | GGACGCACAGGTCAGGTATG | 91 | 163 bp | Hypothetical Protein | GGACGCACAGGTCAGGTATGTAAAAGCAGCCGCAGCAGCAATAACGACTGCCCACCCAGCCCACTTCGGCCAGGCGCCATCTGTTGGCTCCGGAACGGCCACATCCGCTTCAAATCCGGCCAGTGCCGCATCCAGCACCGCCCCCCCTATCACGGTTCCTGCA | 127 |
| Pullorum-1F | 19 | TGCAGGAACCGTGATAGGG | 92 | | | | |

Example 1: Multiple Conventional PCR for Five Salmonella Serovars

Primers for *Salmonella Dublin* and *Salmonella Heidelberg* were modified to allow better band separation on gel, as illustrated in Table 3. DNA from five *Salmonella* serovars, each with the same concentration of ~30 ng/µl, was pooled for running a multiplex PCR. The PCR was performed in three different sets of reactions: Primer set 1 (Set 1) as a triplex, primer set 2 (Set 2) as a duplex and primer set 3 for invA gene (Set 3). The constraint in the use of invA gene in multiplex sets is that the DNA fragment size was too close to that of serovar *Kentucky*, and resolution of more than three bands in one reaction did not turn optimal. Therefore, we decided to use three different tubes, tube one providing three bands for serovars Hadar, *Heidelberg* and *Dublin*; Tube two providing double bands for serovars *Enteritidis* and *Kentucky* and Tube 3 amplifying invA gene that would be run in parallel with the other two tubes. Single PCR reactions for each of the serovars were run along with the multiplex. Set 1 detected Hadar, *Heidelberg* and *Dublin*. The reaction mixture in Set 1 contained 30 µl of reaction volume: 6 µl of PCR grade water, 15 µl of PWO Master Mix and 0.5 µl of each primer (forward and reverse) for *S. hadar, s. heidelberg* and 1 µl of each forward and reverse primer for *S. dublin*. Increasing the concentration of *Dublin* primers to 0.66 µM in the 30 µl reaction volume increased the band intensity for this serovar, and an equal signal band was detected for all the targets while the concentration for other two primers for *S. heidelberg* and *S. hadar* were 0.33 µM. Primer concentrations were adjusted by decreasing those pairs that resulted in relatively strong signal and increasing the ones producing too weak bands in steps of 0.1 µM. This adjustment led to final multiplex system, resulted in equal signal strength for all targets when a mix of standardized template DNA was used.

Set 2 detected *Salmonella* serovars *Enteritidis* and *Kentucky*. The reaction mixture in set 2 contained 20 µl of reaction volume, consisting of 3 µl of PCR grade water, 10 µl of PWO Master Mix and 0.5 µl of forward and reverse primers for *S. enteritidis* and *S. kentucky*. The single PCR reactions for each of the serovars were run with each primer to check the sensitivity of the multiplex PCR and to compare PCR product fragments with those generated from sets 1 and 2. For single serovar PCR, 15 µl reaction volume containing 1.5 µl of PCR grade water, 7.5 µl of PWO Master Mix and 0.5 µl of each forward and reverse primers were used. All PCR reactions were processed using the same program as described above. A mixture of 1 µl of the PCR product, 7 µl of PCR grade water and 2 µl of 6× loading dye was loaded onto 2.5% agarose gel in TAE buffer and ran for 2.5 hours at 100 volts and examined using ALPHAIMAGER (Alpha Innotech® Corporation, San Leandro, Calif.) under ultraviolet light. Annotation and modification of the gel pictures were performed using AlphaView® Software (San Leandro, Calif.).

Figure 3:
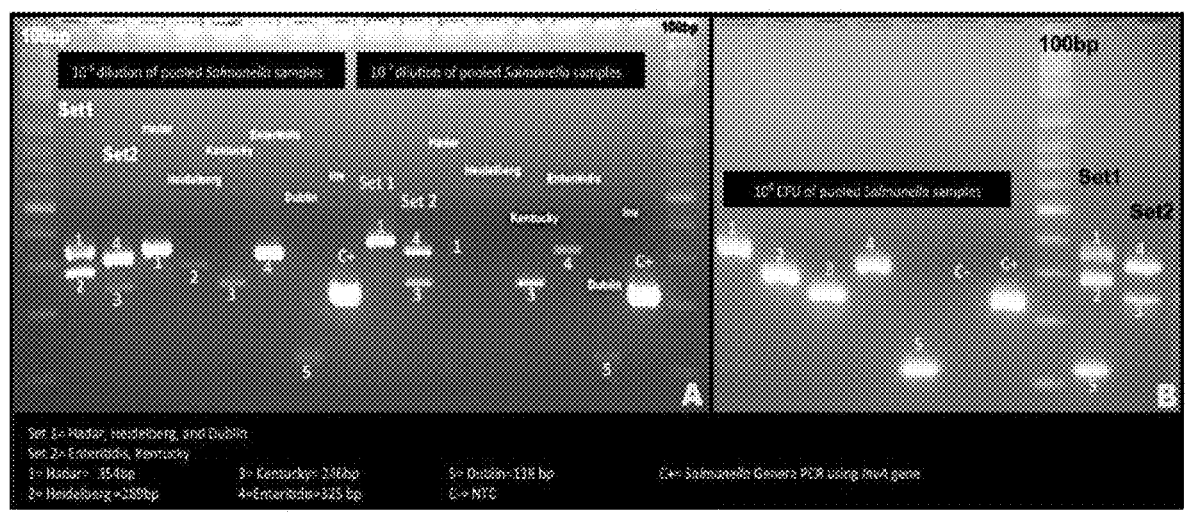
FIG. 3 provides multiplex conventional PCR amplification produced testing the selectivity of various primers developed, including for the detection of serovars *Enteritidis, Heidelberg, Hadar, Kentucky* and *Dublin*, of the five-pooled *Salmonella* serovars serially diluted 10 fold inoculated artificially to milk samples.

The conventional multiplex assay was able to detect serovars Hadar (354 bp fragment), *Heidelberg* (289 bp fragment) and *Dublin* (118 bp fragment) in Set 1 at a DNA concentration of 266 pg/µl. As illustrated in FIG. 3, Set 2 demonstrated detection of serovars *Enteritidis* (325 bp fragment) and *Kentucky* (246 bp fragment) at a DNA concentration of 400 pg/µl. InvA gene and individual serovars were also detected by single PCR primer sets at a DNA concentration of 533 pg/µl per reaction volume.

Similar results were also obtained from artificially contaminated milk samples, as provided below at Examples 4 and 5.

Example 2: Triplex TAQMAN® PCR for Salmonella Serovars

The following experiment was performed to confirm the specificity of Applicants' designed primer pairs to detect by triple TAQMAN® PCR. Due to the limitation of the number of detection filters in the PCR machine, three *Salmonella* serovars, *S. heidelberg, s. enteritidis, s. dublin*, were selected to develop a triplex TAQMAN® assay. An internal positive control (IPC) at 5 fg/25 µl concentration was assigned to one detection filter (VIC). Quantities of DNA used ranged from 30 ng to 15.36 fg ($6*10^6$ to $3*10^0$ Genomic Equivalent, provided by 5 fg of DNA per *E. coli* cell (57) (GE), 2.18 ng to 1.1 fg ($4.36*10^5$ to $3*10$-2GE) and 11 ng to 5.6 fg ($2.2×10^6$ to $1×100$GE) for *S. heidelberg s. dublin* and *S. enteritidis*, respectively. The dyes FAM™, ROX™, CY5™, and JOE™ were used to generate signals for the detection of *S. enteritidis, s. heidelberg, s. dublin* and IPC, respectively. The TAQMAN® assay was operated and analyzed using MxPro® software (Agilent® Technologies Inc., Santa Clara, Calif.). The total volume of reaction was 25 µl consisting of 12.5 µl of 2× Brilliant III QPCR TAQMAN® master mix, 1 µl of 1 µM of each primer, 1 µl of 1 µM of each probe, 2.5 µl of 10×IPC containing primer and probe and 1 µl of DNA from internal positive control and each of the three *Salmonella* serovars. The PCR cycling conditions were 95° C. for 10 minutes followed by 35 cycles of 95° C. for 10 seconds then 60° C. for 1 minute. The result was considered positive when cycle threshold (Ct) value was less than the Ct value of the IPC.

Internal Positive Control.

Internal positive control was used in the TAQMAN® multiplex assay to exclude the presence of PCR inhibitors. For this purpose, an exogenous 10×Exo IPC Mix (VIC) and 50×IPC DNA were purchased from Applied Biosystem (Life Technologies, California, USA). Internal Positive Control detection limit was tested in triplicate to obtain the minimum detection limit by using serially diluted IPC DNA at 80 pg, 16 pg, 3.2 pg, 0.64 pg and 128 µg with constant amount of DNA from *Salmonella* serovars *Heidelberg, Enteritidis*, and *Dublin*. After obtaining the optimal IPC DNA, multiplex TAQMAN® Real Time assay was performed with the target *Salmonella* DNA from serovars *Heidelberg, Enteritidis* and *Dublin* in decreasing concentration to evaluate the optimal co-amplification.

The multiplex TAQMAN® assay was performed to determine the level of detectable DNA and the corresponding genomic equivalent (GE) per ml for each of *S. heidelberg, s. enteritidis* and *S. dublin*. The standard curve was generated using various concentrations of DNA from the three serovars, performed in quadruplet. The slopes for the standard curve of *S. enteritidis* on FAM™, *S. heidelberg* on ROX™ and *S. dublin* on CY5™ were –3.460, –3.592 and –4.093, respectively. The regression curves were generated for these three serovars based on the varying amounts of bacterial DNA. A good linearity response was shown for each of the standard curves of the serovars. The R2 value was 1.000 for *S. enteritidis*, 0.998 for *S. heidelberg* and 0.992 for *S. dublin*. The results indicated that the multiplex Real-Time PCR successfully detected the minimum amount of DNA in the assay and corresponding GE/ml, which was 75.8 fg ($1.53*10^1$) for *S. heidelberg*, 140.8 fg ($2.8*10^1$) for *S. enteritidis*, and 3.48 pg ($6.96*10^2$) for *S. dublin*. PCR efficiencies calculated from the standard curve gave efficiency of 89.8% for *S. heidelberg*; 94.5% for *Enteritidis*, and 75.5% for *S. dublin*.

As illustrated in FIG. 3, the current study successfully developed a multiplex conventional PCR assay that was able to detect five *Salmonella* serovars in three sets of PCR reactions run in parallel. The multiplex TAQMAN® assay developed in this study also successfully detected a small amount of DNA from serovars *Heidelberg, Enteritidis* and *Dublin*. In previous studies, real-time PCR assay was used only for identification of *Salmonella* at species level or other foodborne pathogens (23, 24, 48) or only for detecting one or two serovars (10, 51, 54).

Example 3: Determination of the Sensitivity and Efficiency

The following experiment was conducted to test the sensitivity and efficiency of each of the primers identified in Table 3. The sensitivity of the TAQMAN® assay was determined by five-fold serial dilution of the genomic DNA of each of the target *Salmonella* serovar. The PCR was done in quadruplicate to plot the standard curve and evaluate both the sensitivity and the reaction efficiency. Each of the reactions contained the IPC. PCR efficiency was calculated from the standard curves using the formula $E=(10-1/slope-1)\times 100$.

SYBR Green Real Time PCR was performed to determine the detection limit for the five serovars. The sensitivities for DNA detection were found to be 58.8 fg/tl for *S. heidelberg*, 42.2 fg/tl for *S. kentucky*, 200 fg/tl for *S. hadar*, 63.4 fg/tl for *S. enteritidis* and 26 pg/tl for *S. dublin*, which corresponded with ~11.8, 8.4, 40, 13, 5200 CFU/ml, respectively.

Therefore, under these conditions, Applicants found that these five primers were able to achieve a high sensitivity of detection combined with the high specificity as described above. Similar sensitivity assays of various other primers achieved results confirming them as having suitable sensitivities for use.

This sensitivity assay was very sensitive detecting femto gram amounts of DNA for serovars Hadar, *Heidelberg, Kentucky, Enteritidis* and pictogram levels of DNA for *S. dublin*. The lower sensitivity for *Dublin* may be explained in part by the fact that we used whole genome extraction kit because most of the DNAs in the current study were of bacterial genomic 467 origin. As observed by others, plasmids could be depleted during extractions with salting-out kits except for larger plasmids of 362 kb (3). The use of plasmid extraction kit later in the study resulted a band with higher signal with *S. dublin* (data not shown). *S. dublin* has an 80 kb plasmid that is responsible for systemic infection in cattle (12) and causes high mortality. On the other hand, plasmid-free strains cause less severe conditions and are responsible for only enteric infection. The virulent plasmid is very conserved in the host cell (37) and is necessary for its pathogenesis. This plasmid has efficient stability with an estimated loss less than 10-7 per generation per cell (11). The stability of the *S. dublin* plasmid depends on a multimer resolution system that consists of a resolvase, encoded by the crs gene, and a resolution site, rsd. This system is also present in other *Salmonella* plasmids. A locus called vagC/vagD may also be involved in the maintenance of the *S. dublin* plasmid; delaying cell division until replication has been completed (18, 37, 56, 67). This is the primary reason why plasmid bearing *S. dublin* was targeted in Applicants' study.

Example 4: Artificial Contamination of Food Samples

Food matrices provide a critical challenge in amplification-based pathogen detection approaches because, among other things, pre-analytical sample processing techniques must be streamlined to reduce the time needed to arrive at diagnosis and decision-making. In this experiment, Applicants performed a preliminary experiment to evaluate the real time detection of S. serovars spiked in milk to evaluate whether real-time detection as described herein would be compatible with DNA isolated from bacteria in food matrix.

Milk samples including whole milk, 2% fat, fat free and chocolate milk were confirmed *Salmonella*-free by standard cultural method (47) where 25 ml milk sample was pre-enriched in 225 ml of Buffered Peptone Water at 37° C. for 20 h. Equal amounts of overnight cultures of *S. heidelberg, s. hadar, s. kentucky, s. enteritidis* and *S. dublin* were pooled after each serovar was adjusted to same OD value of 0.5 using NANODROP 2000C spectrophotometers. The pooled samples were then 10-fold serially diluted up to 108. Each dilution was plated on both Tryptic Soya agar and XLT4 media to evaluate the number of colony forming units (CFU). Serially diluted pooled bacteria were used to artificially inoculate the *Salmonella*-free milk. Briefly 25 ml of milk was transferred into sterile Nasco Whirl-Pak® (Universal Medical Inc, Norwood, USA) containing 225 ml of sterile BPW and inoculated with pooled cultures containing 0 CFU to $1\times 10^7$ CFU. The mixture was homogenized with Stomacher® 400 Circulator (Seward Laboratory Systems Inc., Florida, USA) and incubated at 37° C. for 20 h for pre-enrichment. After pre-enrichment, 100 µL of the pre-enriched sample was inoculated into 10 ml of RVS and incubated at 41.5° C. for 12 h. DNA was extracted from RVS (selective enriched) and stored at −20° C. for further use.

Example 5: Detection of Natural Contamination of *Salmonella* from Milk and Chicken Meat Samples Thirty pasteurized milk and thirty raw chicken samples were sourced from different suppliers to for the presence of *Salmonella* using the newly developed PCR assay. Different types of milk samples were collected from different brands. The raw chicken samples were from wings, necks, gizzards, and leg quarters. Twenty-five grams of meat from each sample were weighed and added to 225 ml of BPW then homogenized with a Stomacher® 400 Circulator machine. For the milk samples, 25 ml were measured and processed using the same procedure as used for chicken samples. The homogenized samples were then incubated at 37° C. for 20 h after which 100 µl of each pre-enriched sample was transferred into 10 ml of RVS and incubated at 41.5° C. for 12 h. DNA was extracted from 1 ml of the RVS cultures and kept at −20° C. until further use.

Figure 4:
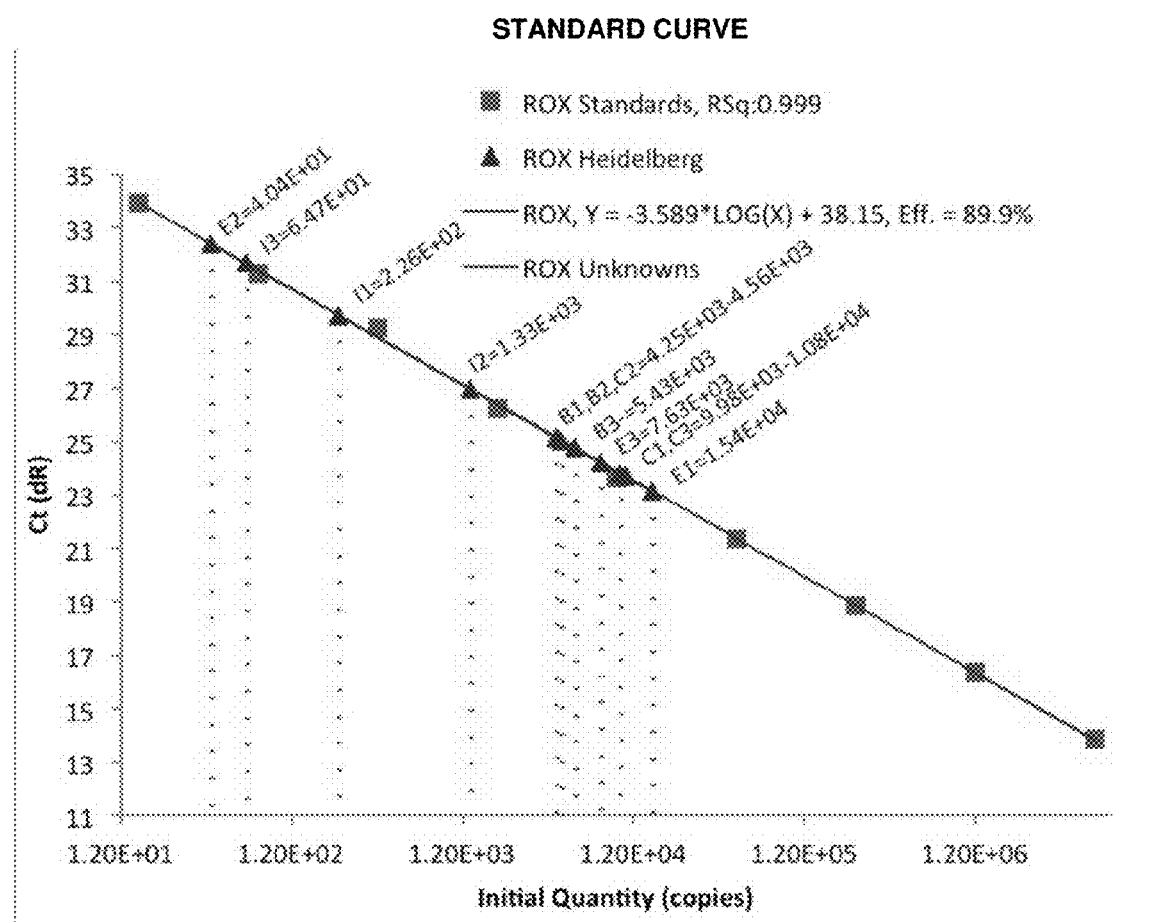
FIG. 4 provides TAQMAN® PCR results for detecting and quantification of *Salmonella Heidelberg* from naturally contaminated chicken samples obtained from retail supermarkets using embodiments of the present invention.
Figure 5:
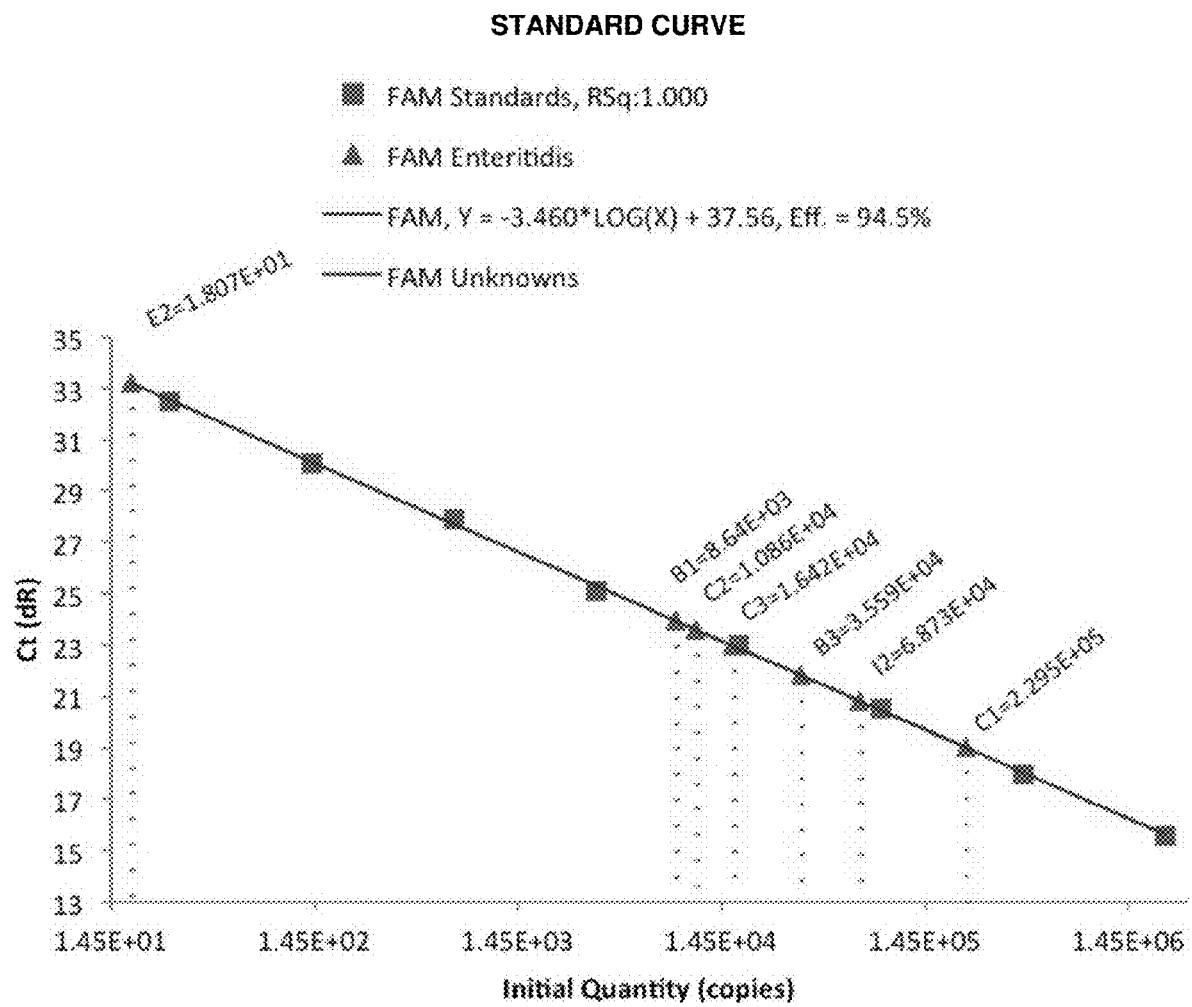
FIG. 5 illustrates the detection and quantification of *Salmonella Enteritidis* from naturally contaminated chicken samples obtained from retail supermarkets using TAQMAN® assay, after enrichment steps. Quantitative assay determined minimum amount of 18 CFU of *Salmonella Enteritidis* from sample number E2 at around 33 cycles, and maximum amount of *Salmonella Enteritidis* contamination was observed from sample number C1 giving $2.3 \times 10^5$ CFU.
Figure 6:
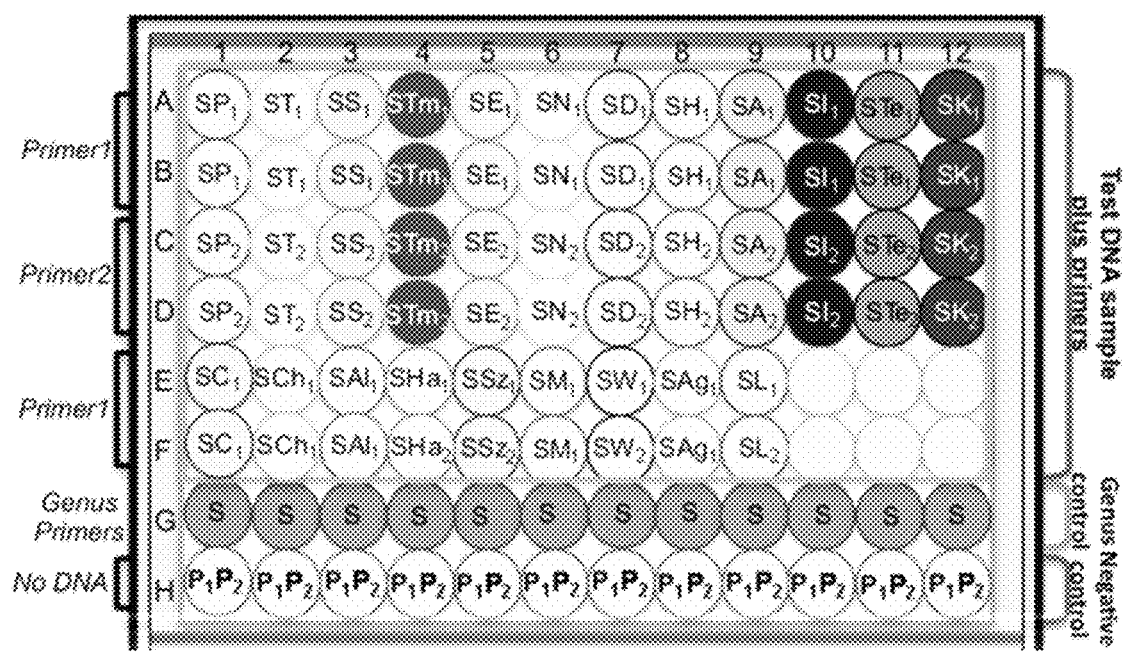
FIG. 6 illustrates an example of a multiple multiplex serovar microarray with two or more primer pairs placed on a microplate for receiving test samples.

The purpose of analyzing the milk samples was to test if *Salmonella* could be detected in commercial dairy products. All milk samples tested negative for *Salmonella* using both culture and PCR. As provided in Table 4, among the thirty chicken samples, twelve (40%) were positive by both cultural and conventional PCR targeting the *Salmonella* specific invA gene. Those twelve positive samples were individually tested by conventional PCR using our serovar-specific primers (data not shown). The result of serovar-specific PCR showed six positive samples (20.0% of the total 30 samples) for serovar *Kentucky* (B1, B2, B3, C1, C2 and C3). Analysis using the *S. enteritidis*-specific PCR revealed seven positive samples (20% of the total) for *S. enteritidis* (B1, B3, C1, C2, C3 and 12). Results also showed that five of the 30 samples (16.6%) (B1, B3, C1, C2 and C3) were dually contaminated with both *S. kentucky* and *S. enteritidis*. Tests using the *S. heidelberg*-specific PCR primers did not detect any of the twelve samples as positive. Using the TAQMAN® assay, targeting only *S. heidelberg, s. enteritidis* and *S. dublin*, same results were obtained as in the conventional PCR for *S. enteritidis* and *S. dublin*. However, this assay also amplified eleven samples (out of the 30 total) as *S. heidelberg*, among which six were co-detected with serovar *Enteritidis* (FIGS. 4 and 5). Single colonies randomly picked from all the twelve positive samples were sent to USDA laboratory, Athens, Ga. for further identification. Briefly, the method involved extraction of DNA from purified colonies inoculated on Brilliant Green Sulpha agarose (Hardy Diagnostics®, Santa Maria, Calif.), followed by amplification and sequencing of Intergenic sequence ribotyping (ISR) to evaluate single nucleotide polymorphisms occurring in a 5S ribosomal gene region and flanking sequences bordering the gene dkgB (26). The laboratory confirmed five samples (B1, B2, C1, C2 and C3) as *S. kentucky*, which was also detected by our assays as *S. kentucky*. It is possible that serovar *Kentucky* colony was not picked or was likely over grown by other non-*Salmonella* organisms, which could explain absence of *Kentucky* in sample B3. It is also important to remember that organisms that are viable but none-cultivable (VBNC) could be missed in culturing step but their genomic DNA could easily be amplified by PCR directly from the RV broth (19). The USDA laboratory also detected I1, I2 and I3 as *Typhimurium*, but *Typhimurium* primers were not used in the present assay, although we have already developed and validated specific *S. Typhimurium* primers in our previous work (65), Table 5 presents comparison of results obtained using the two approaches.

FIGS. 4 and 5 illustrate the standard curve method was used to estimate the initial concentration of both *S. enteritidis* and *S. heidelberg* in all the positive samples. Results showed that minimum numbers of *S. enteritidis* detected from the meat samples were approximately 18 cells (sample E2) and that of *S. heidelberg* were 40 cells (sample E2), respectively.

The multiplex conventional assay and multiplex TAQMAN® assay developed were sensitive enough to successfully detect 1 to 10 CFU from artificially inoculated milk after enrichment. Both multiplex conventional and TAQMAN® assay also yielded 100% similar results. The use of Internal Positive Control (IPC) in the TAQMAN® assay made the assay more robust and reliable. IPC is required to exclude the presence of PCR inhibitors and also to check the quality of PCR reagents and thermal cycler conditions (30).

Results from our experiments to detect natural contamination of chicken samples using our new assay proved to be successful, as the bacteria isolated as *S. kentucky* was also confirmed by sequencing in USDA laboratory at Athens, Ga. This gives further confidence that the developed assay is very reliable to detect the contamination from different food samples and therefore from potential outbreak samples directly from RV broth. This study detected multiple *Salmonella* contaminations of single food source, which were not otherwise detected by randomly selected colonies from *Salmonella* specific plates. In this study, we also observed that TAQMAN® assay was more sensitive than conventional PCR assay. Unlike the TAQMAN® assay, conventional assay could not detect *S. heidelberg* and *S. enteritidis* from naturally contaminated chicken samples. This finding is supported by others who had reported TAQMAN® assay is more sensitive than conventional PCR assay (2, 22).

The assay developed in this study employs unique targets for the serovars *Heidelberg*, Hadar, *Enteritidis, Kentucky* and *Dublin*, all of which are important from public health and economic perspectives in the USA and worldwide. However, we strongly believe the conventional multiplex PCR assay will be a valuable tool for diagnostic laboratories as well as for other food processing units to detect in a single run these five major *Salmonella* serovars. This tool would be also very helpful for low resource environment where Real Time PCR may not be possible. Also the TAQMAN® assay will be a useful tool for the detection and quantitation of serovars *Heidelberg, Enteritidis* and *Dublin*. Finally, we believe that our developed assays would be useful for routine laboratory diagnosis of *Salmonella*, as well as for rapid diagnostic testing during an outbreak. These developments could replace the conventional diagnostic technique that requires almost 7 days, while the assay developed here requires only one or two days.

In this manner, the experiments described herein demonstrate the suitability of the various assays, kits and primers discovered by Applicants for combined simultaneous use in real-time PCR screens for detecting and identifying *Salmonella* serovars as food threat agents and food-borne pathogens with levels of specificity and sensitivity not previously obtained by others in the art.

Having described preferred embodiments of the invention; it will now become apparent to those of ordinary skill in the art that other embodiments incorporating these concepts may be used. Accordingly, it is submitted that that the invention should not be limited to the described embodiments but rather should be limited only by the spirit and scope of the appended claims.

Although the invention has been described and illustrated with a certain degree of particularity, it is understood that the present disclosure has been made only by way of example, and that numerous changes in the combination and arrangement of steps, ingredients, or processes can be resorted to by those skilled in the art without departing from the spirit and scope of the invention, as will be claimed hereafter.

TABLE 4

Detection of invA gene, *Salmonella* Heidleberg, *Salmonella Enteritidis*, and *Salmonella* Dublin from commercially obtained chicken samples

| | | PCR results | | | | |
|---|---|---|---|---|---|---|
| | | | TaqMan assay | | | |
| | Conventional | *Salmonella Eteritidis* | | *Salmonella Heidelberg* | | *Salmonella* Dublin |
| Sample ID | (invA) | $C_T$ | GE/mL[a] | $C_T$ | GE/mL | $C_T$ |
| B1 | + | 23.94 | $1.727 \times 10^6$ | 25.13 | $8.494 \times 10^5$ | — |
| B2 | + | — | | — | | — |
| B3 | + | 21.81 | $7.118 \times 10^6$ | 24.74 | $1.087 \times 10^6$ | — |
| C1 | + | 19.01 | $4.59 \times 10^7$ | 23.8 | $1.997 \times 10^6$ | — |
| C2 | + | 23.6 | $2.172 \times 10^6$ | 25.02 | $9.114 \times 10^5$ | — |
| C3 | + | 22.97 | $3.284 \times 10^6$ | — | | — |
| E1 | + | — | | 23.12 | $3074 \times 10^5$ | — |
| E2 | + | — | | 32.39 | $8.08 \times 10^3$ | — |
| E3 | + | — | | 24.22 | $1.527 \times 10^6$ | — |
| I1 | + | — | | 29.7 | $4.512 \times 10^4$ | — |
| I2 | + | 20.82 | $1.37 \times 10^7$ | 26.93 | $2.668 \times 10^5$ | — |
| I3 | + | — | | 31.65 | $1.294 \times 10^4$ | — |

GE = Genomic Equivalent, Genomic Equivalent, provided by 5 fg of DNA per *E. coli* cell (54)
[a] The number of GE/ml of enriched sample was determined by comparing the CT value to the standard curve and then multiplying the GE by 100 as 1 μl of 200 μl DNA which was extracted from 1 ml of sample was used in the TaqMan PCR assay for natural contamination

TABLE 5

Detection of *Salmonella* serovars from commercial chicken samples by using conventional and TaqMan PCR assays and ISR-specific sequencing[3]

| Sample ID | *Salmonella* serovars detected PCR assays | ISR sequencing |
|---|---|---|
| B1 | Kentucky, Enteritidis, and Heidelberg | Kentucky |
| B2 | Kentucky and Heidelberg | Kentucky |
| B3 | Kentucky, Enteritidis, and Heidelberg | Not *Salmonella* |
| C1 | Kentucky Enteritidis, and Heidelberg | Kentucky |
| C2 | Kentucky and Heidelberg | Kentucky |
| C3 | Kentucky, Enteritidis, and Heidelberg | Kentucky |
| E1 | Heidelberg | Not *Salmonella* |
| E2 | Heidelberg | Not *Salmonella* |
| E3 | | Not *Salmonella* |
| I1 | Heidelberg and Enteritidis | Typhimurium |
| I2 | Enteritidis and Heidelberg | Typhimurium |
| I3 | Heidelberg | Typhimurium |

[3] Conventional and TaqMan PCR assays were conducted in our laboratory, and ISR-specific sequencing was conducted at the USDA laboratory (Athens, GA).

REFERENCES

1. Abubakar, I., L. Irvine, C. F. Aldus, G. M. Wyatt, R. Fordham, S. Schelenz, L. Shepstone, A. Howe, M. Peck, and P. R. Hunter. 2007. A systematic review of the clinical, public health and cost-effectiveness of rapid diagnostic tests for the detection and identification of bacterial intestinal pathogens in faeces and food. Health Technol Assess. 11:1-216.
2. Balamurugan, V., K. D. Jayappa, M. Hosamani, V. Bhanuprakash, G. Venkatesan, and R. K. Singh. 2009. Comparative efficacy of conventional and TaqMan polymerase chain reaction assays in the detection of capripoxviruses from clinical samples. Journal of veterinary diagnostic investigation. 21:225-231.
3. Becker, L., M. Steglich, S. Fuchs, G. Werner, and U. Nübel. 2016. Comparison of six commercial kits to extract bacterial chromosome and plasmid DNA for MiSeq sequencing. Scientific Reports. 6:28063.
4. Braden, C. R. 2006. *Salmonella enterica* serotype *Enteritidis* and eggs: a national epidemic in the United States. Clin Infect Dis. 43:512-7.
5. Bugarel, M., A. Tudor, G. H. Loneragan, and K. K. Nightingale. 2017. Molecular detection assay of five *Salmonella* serotypes of public interest: *Typhimurium, Enteritidis*, Newport, *Heidelberg*, and Hadar. J Microbiol Methods. 134:14-20.
6. CDC. 1984. *Salmonella Dublin* and raw milk consumption California. MMWR. 33:196-8.
7. CDC. 2003. *Salmonella* Surveillance Summary, 2002. In US Department of Health and Human Services (ed.) CDC, Atlanta, Ga.
8. CDC. 2014. Notes from the Field: Multistate Outbreak of Human *Salmonella* Infections Linked to Live Poultry from a Mail-Order Hatchery in Ohio March-September 2013. p. 222. In, MMWR, vol. 63.
9. Cernela, N., M. Nüesch-Inderbinen, H. Hächler, and R. Stephan. 2014. Antimicrobial resistance patterns and genotypes of *Salmonella enterica* serovar Hadar strains associated with human infections in Switzerland, 2005-2010. Epidemiology and infection. 142:84-89.
10. Chen, J., L. Zhang, G. C. Paoli, C. Shi, S.-I. Tu, and X. Shi. 2010. A real-time PCR method for the detection of *Salmonella enterica* from food using a target sequence identified by comparative genomic analysis. International journal of food microbiology. 137:168-174.
11. Chikami, G. K., J. Fierer, and D. G. Guiney. 1985. Plasmid-Mediated Virulence in *Salmonella Dublin* Demonstrated by Use of a Tn5-oriT Construct. American Society for Microbiology. 50:420-424.
12. Chu, C., Y. Feng, A.-C. Chien, S. Hu, C.-H. Chu, and C.-H. Chiu. 2008. Evolution of genes on the *Salmonella* Virulence plasmid phylogeny revealed from sequencing of the virulence plasmids of *S. enterica* serotype *Dublin* and comparative analysis. Genomics. 92:339-343.
13. Demczuk, W., G. Soule, C. Clark, H.-W. Ackermann, R. Easy, R. Khakhria, F. Rodgers, and R. Ahmed. 2003. Phage-based typing scheme for *Salmonella enterica* serovar *Heidelberg*, a causative agent of food poisonings in Canada. Journal of clinical microbiology. 41:4279-4284.

14. Dietz, H. H., M. Chriél, T. H. Andersen, J. C. Jorgensen, M. Torpdahl, H. Pedersen, and K. Pedersen. 2006. Outbreak of *Salmonella Dublin*-associated abortion in Danish fur farms. Canadian veterinary journal. 47:1201.
15. Dinjus, U., I. Hanel, W. Müller, R. Bauerfeind, and R. Helmuth. 1997. Detection of the induction of *Salmonella* enterotoxin gene expression by contact with epithelial cells with RT-PCR. FEMS microbiology letters. 146:175-179.
16. Doran, J. L., S. K. Collinson, C. M. Kay, P. A. Banser, J. Burian, C. K. Munro, S. H. Lee, J. M. Somers, E. C. Todd, and W. W. Kay. 1994. fimA and tctC based DNA diagnostics for *Salmonella*. Mol Cell Probes. 8:291-310.
17. DuPont, H. L. 2007. The growing threat of foodborne bacterial enteropathogens of animal origin. Clinical infectious diseases. 45:1353-1361.
18. Ebersbach, G., and K. Gerdes. 2005. Plasmid segregation mechanisms. Annu Rev Genet. 39:453-79.
19. Fakruddin, M., K. S. B. Mannan, and S. Andrews. 2013. Viable but Nonculturable Bacteria: Food Safety and Public Health Perspective. ISRN Microbiology. 2013:6.
20. Ferretti, R., Mannazzu, I, Cocolin, Luca, Comi, Giuseppe, & Clementi, Francesca. 2001. Twelve-hour PCR-based method for detection of *Salmonella* spp. in food. Applied and environmental microbiology. 67(2) 977-978.
21. Fricke, W. F., P. F. McDermott, M. K. Mammel, S. Zhao, T. J. Johnson, D. A. Rasko, P. J. Fedorka-Cray, A. Pedroso, J. M. Whichard, J. E. LeClerc, D. G. White, T. A. Cebula, and J. Ravel. 2009. Antimicrobial Resistance-Conferring Plasmids with Similarity to Virulence Plasmids from Avian Pathogenic *Escherichia coli* Strains in *Salmonella enterica* Serovar *Kentucky* Isolates from Poultry. Applied and Environmental Microbiology. 75:5963-5971.
22. Garland, S., J. Wood, and L. F. Skerratt. 2011. Comparison of sensitivity between real-time detection of a TaqMan assay for Batrachochytrium dendrobatidis and conventional detection. Dis Aquat Organ. 94:101-5.
23. Gillespie, B., and S. Oliver. 2005. Simultaneous detection of mastitis pathogens, *Staphylococcus aureus, Streptococcus uberis*, and *Streptococcus agalactiae* by multiplex real-time polymerase chain reaction. Journal of dairy science. 88:3510-3518.
24. Grant, M. A., J. Hu, and K. C. Jinneman. 2006. Multiplex real-time PCR detection of heat-labile and heat-stable toxin genes in enterotoxigenic *Escherichia coli*. Journal of Food Protection®. 69:412-416.
25. Greene, H., and D. Dempsey. 1986. Bovine neonatal *salmonellosis*: An outbreak in a dairy calf rearing unit. Irish Veterinary Journal. 40:30-34.
26. Guard, J., R. Sanchez-Ingunza, C. Morales, T. Stewart, K. Liljebjelke, J. Van Kessel, K. Ingram, D. Jones, C. Jackson, P. Fedorka-Cray, J. Frye, R. Gast, and A. Hinton, Jr. 2012. Comparison of dkgB-linked intergenic sequence ribotyping to DNA microarray hybridization for assigning serotype to *Salmonella enterica*. FEMS Microbiol Lett. 337:61-72.
27. Guo, X., J. Chen, L. R. Beuchat, and R. E. Brackett. 2000. PCR Detection of *Salmonella* entericaSerotype Montevideo in and on Raw Tomatoes Using Primers Derived from hilA. Applied and environmental microbiology. 66:5248-5252.
28. Hadjinicolaou, A. V., V. L. Demetriou, M. A. Emmanuel, C. K. Kakoyiannis, and L. G. Kostrikis. 2009. Molecular beacon-based real-time PCR detection of primary isolates of *Salmonella Typhimurium* and *Salmonella Enteritidis* in environmental and clinical samples. BMC Microbiol. 9:97.
29. Hohmann, E. L. 2001. Nontyphoidal *salmonellosis*. Clin Infect Dis. 32:263-9.
30. Hoorfar J, C. N., Malorny B, Wagner M, De Medici D, Abdulmawjood A, Fach P. 2004. Diagnostic PCR: making internal amplification control mandatory. J Appl Microbiol. 96(2).
31. ISO. 2003. ISO 6579:2002. In, Microbiology of food and animal feeding stuffs. Horizontal method for the detection of *Salmonella* spp.
32. Jackson, B. R., P. M. Griffin, D. Cole, K. A. Walsh, and S. J. Chai. 2013. Outbreak-associated *Salmonella enterica* serotypes and food Commodities, United States, 1998-2008. Emerg Infect Dis. 19:1239-44.
33. Kim, H., S. Park, T. Lee, B. Nahm, Y. Chung, K. Seo, and H. Kim. 2006. Identification of *Salmonella enterica* serovar *Typhimurium* using specific PCR primers obtained by comparative genomics in *Salmonella* serovars. Journal of Food Protection®. 69:1653-1661.
34. Kim, H.-J., S.-H. Park, T.-H. Lee, B.-H. Nahm, Y.-R. Kim, and H.-Y. Kim. 2008. Microarray detection of food-borne pathogens using specific probes prepared by comparative genomics. Biosensors and Bioelectronics. 24:238-246.
35. Kimura, A. C., V. Reddy, R. Marcus, P. R. Cieslak, J. C. Mohle-Boetani, H. D. Kassenborg, S. D. Segler, F. P. Hardnett, T. Barrett, and D. L. Swerdlow. 2004. Chicken consumption is a newly identified risk factor for sporadic *Salmonella enterica* serotype *Enteritidis* infections in the United States: a case-control study in FoodNet sites. Clinical Infectious Diseases. 38:S244-S252.
36. Kingsley, R. A., and A. J. Balmier. 2000. Host adaptation and the emergence of infectious disease: the *Salmonella* paradigm. Molecular microbiology. 36:1006-1014.
37. Krause, M., and D. G. Guiney. 1991. Identification of a multimer resolution system involved in stabilization of the *Salmonella dublin* virulence plasmid pSDL2. Journal of Bacteriology. 173:5754-5762.
38. Kubota, K., E. Iwasaki, S. Inagaki, T. Nokubo, Y. Sakurai, M. Komatsu, H. Toyofuku, F. Kasuga, F. J. Angulo, and K. Morikawa. 2008. The human health burden of foodborne infections caused by *Campylobacter, Salmonella*, and *Vibrio parahaemolyticus* in Miyagi Prefecture, Japan. Foodborne Pathog Dis. 5:641-8.
39. Lampel, K., S. Keasler, and D. Hanes. 1996. Specific detection of *Salmonella enterica* serotype *Enteritidis* using the polymerase chain reaction. Epidemiology and infection. 116:137-145.
40. Le Hello, S., A. Bekhit, S. A. Granier, H. Barua, J. Beutlich, M. Zajac, S. Munch, V. Sintchenko, B. Bouchrif, K. Fashae, J. L. Pinsard, L. Sontag, L. Fabre, M. Gamier, V. Guibert, P. Howard, R. S. Hendriksen, J. P. Christensen, P. K. Biswas, A. Cloeckaert, W. Rabsch, D. Wasyl, B. Doublet, and F. X. Weill. 2013. The global establishment of a highly-fluoroquinolone resistant *Salmonella enterica* serotype *Kentucky* ST198 strain. Front Microbiol. 4:395.
41. Le Hello, S., D. Harrois, B. Bouchrif, L. Sontag, D. Elhani, V. Guibert, K. Zerouali, and F. X. Weill. 2013. Highly drug-resistant *Salmonella enterica* serotype *Kentucky* ST198-X1: a microbiological study. Lancet Infect Dis. 13:672-9.
42. Le Hello, S., R. S. Hendriksen, B. Doublet, I. Fisher, E. M. Nielsen, J. M. Whichard, B. Bouchrif, K. Fashae, S. A. Granier, N. Jourdan-Da Silva, A. Cloeckaert, E. J. Threlfall, F. J. Angulo, F. M. Aarestrup, J. Wain, and F.-X. Weill. 2011. International Spread of an Epidemic Population of *Salmonella enterica* Serotype *Kentucky* ST198 Resistant to Ciprofloxacin. Journal of Infectious Diseases.
43. Liu, Z. M., X. M. Shi, and F. Pan. 2007. Species-specific diagnostic marker for rapid identification of *Staphylococcus aureus*. Diagn Microbiol Infect Dis. 59:379-82.
44. Majowicz, S. E., J. Musto, E. Scallan, F. J. Angulo, M. Kirk, S. J. O'Brien, T. F. Jones, A. Fazil, and R. M. Hoekstra. 2010. The global burden of nontyphoidal *Salmonella* gastroenteritis. Clinical Infectious Diseases. 50:882-889.
45. Malorny, B., C. Bunge, and R. Helmuth. 2007. A real-time PCR for the detection of *Salmonella Enteritidis* in poultry meat and consumption eggs. J Microbiol Methods. 70.
46. Malorny, B., J. Hoorfar, C. Bunge, and R. Helmuth. 2003. Multicenter validation of the analytical accuracy of *Salmonella* PCR: towards an international standard. Applied and environmental microbiology. 69:290-296.
47. Malorny, B., D. Made, and C. Löfström. 2013. Real-time PCR Detection of Food-borne Pathogenic *Salmonella* spp. p. 57-77. In D. Rodriguez-Lázaro (ed.), Real-Time PCR in Food Science: Current Technology and Applications Caister Academic Press.
48. Malorny, B., E. Paccassoni, P. Fach, C. Bunge, A. Martin, and R. Helmuth. 2004. Diagnostic real-time PCR for detection of *Salmonella* in food. Appl Environ Microbiol. 70:7046-52.
49. Marcus, R., J. Varma, C. Medus, E. Boothe, B. Anderson, T. Crume, K. Fullerton, M. Moore, P. White, and E. Lyszkowicz. 2007. Re-assessment of risk factors for sporadic *Salmonella* serotype *Enteritidis* infections: a case-control study in five FoodNet Sites, 2002— 2003. Epidemiology and Infection. 135:84-92.
50. Mateus, A., D. J. Taylor, D. Brown, D. J. Mellor, R. Bexiga, and K. Ellis. 2008. Looking for the unusual suspects: a *Salmonella Dublin* outbreak investigation. Public Health. 122:1321-3.
51. Maurischat, S., B. Baumann, A. Martin, and B. Malorny. 2015. Rapid detection and specific differentiation of *Salmonella enterica* subsp. *enterica Enteritidis, Typhimurium* and its monophasic variant 4,[5], 12: i:—by real-time multiplex PCR. International journal of food microbiology. 193:8-14.
52. Murugkar, H. V., H. Rahman, and P. K. Dutta. 2003. Distribution of virulence genes I *Salmonella* serovars isolated from man & animals. Indian J Med Res. 117:66-70.
53. Nielsen, L. R., B. van den Borne, and G. van Schaik. 2007. *Salmonella Dublin* infection in young dairy calves: transmission parameters estimated from field data and an SIR-model. Prev Vet Med. 79:46-58.
54. O'Regan, E., E. McCabe, C. Burgess, S. McGuinness, T. Barry, G. Duffy, P. Whyte, and S. Fanning. 2008. Development of a real-time multiplex PCR assay for the detection of multiple *Salmonella* serotypes in chicken samples. BMC microbiology. 8:156.
55. Ou, H. Y., C. T. Ju, K. L. Thong, N. Ahmad, Z. Deng, M. R. Barer, and K. Rajakumar. 2007. Translational genomics to develop a *Salmonella enterica* serovar Paratyphi A multiplex polymerase chain reaction assay. J Mol Diagn. 9:624-30.
56. Pullinger, G. D., and A. J. Lax. 1992. A *Salmonella Dublin* virulence plasmic locus that affects bacterial growth under nutrient-limited conditions. Molecular Microbiology. 6:1631-1643.
57. Raghunathan, A., H. R. Ferguson, Jr., C. J. Bornarth, W. Song, M. Driscoll, and R. S. Lasken. 2005. Genomic DNA amplification from a single bacterium. Appl Environ Microbiol. 71:3342-7.
58. Sint, D., L. Raso, and M. Traugott. 2012. Advances in multiplex PCR: balancing primer efficiencies and improving detection success. Methods in Ecology and Evolution. 3:898-905.
59. Sivapalasingam, S., C. R. Friedman, L. Cohen, and R. V. Tauxe. 2004. Fresh produce: a growing cause of outbreaks of foodborne illness in the United States, 1973 through 1997. Journal of Food Protection®. 67:2342-2353.
60. Song, J.-H., H. Cho, M. Y. Park, Y. S. Kim, H. B. Moon, Y. K. Kim, and C. H. Pai. 1994. Detection of the H1-j strain of *Salmonella typhi* among Korean isolates by the polymerase chain reaction. The American journal of tropical medicine and hygiene. 50:608-611.
61. Uzzau, S., D. J. Brown, T. Wallis, S. Rubino, G. Leori, S. Bernard, J. Casadesús, D. J. Platt, and J. E. Olsen. 2000. Host adapted serotypes of *Salmonella enterica*. Epidemiology and infection. 125:229-255.
62. Vandegraaff, R., and J. Malmo. 1977. *Salmonella Dublin* in dairy cattle. Australian veterinary journal. 53:453-455.
63. Voetsch, A. C., T. J. Van Gilder, F. J. Angulo, M. M. Farley, S. Shallow, R. Marcus, P. R. Cieslak, V. C. Deneen, R. V. Tauxe, and G. Emerging Infections Program FoodNet Working. 2004. FoodNet estimate of the burden of illness caused by nontyphoidal *Salmonella* infections in the United States. Clin Infect Dis. 38 Suppl 3:S127-34.
64. Wattam, A. R., J. J. Davis, R. Assaf, S. Boisvert, T. Brettin, C. Bun, N. Conrad, E. M. Dietrich, T. Disz, J. L. Gabbard, S. Gerdes, C. S. Henry, R. W. Kenyon, D. Machi, C. Mao, E. K. Nordberg, G. J. Olsen, D. E. Murphy-Olson, R. Olson, R. Overbeek, B. Parrello, G. D. Pusch, M. Shukla, V. Vonstein, A. Warren, F. Xia, H. Yoo, and R. L. Stevens. 2017. Improvements to PATRIC, the all-bacterial Bioinformatics Database and Analysis Resource Center. Nucleic Acids Res. 45:D535-D542.
65. Woubit, A. S., T. Yehualaeshet, T. Habtemariam, and T. Samuel. 2012. Simultaneous, specific and real-time detection of biothreat and frequently encountered food-borne pathogens. Journal of food protection. 75:660-670.
66. Wray, C., and W. J. Sojka. 1977. Bovine *salmonellosis*. Journal of Dairy Research. 44:383-425.
67. Yarmolinsky, M. B. 1995. Programmed cell death in bacterial populations. Science. 267:836-7.

The invention claimed is:

1. A multiplex real-time PCR system for use in simultaneously testing for a plurality of *Salmonella* serovars that are foodborne pathogens or food threat agents, said system comprising:
   a container for receiving test samples, said container containing two or more primer pairs, said two or more primer pairs being adapted to detect and distinguish with specificity DNA from at least two different *Salmonella* serovars that are foodborne pathogens or food threat agents,
   wherein all said primer pairs have similar melting temperatures such that they can be simultaneously run under the same polymerase chain reaction (PCR) conditions, and wherein said primer pairs comprise at least one primer selected from SEQ ID NO: 1 and SEQ ID NO: 2,
   wherein the container further contains a different oligonucleotide probe for each primer pair, the oligonucleotide probes each being designed to bind to DNA regions flanked by the regions in genomes of the at least two different *Salmonella* serovars targeted by the primer pairs, each probe labeled with a different reporter dye having emission capabilities distinguishable from other ones of said probes.

2. The system according to claim 1, wherein said probes are capable of selectively detecting two or more target microorganisms selected from the group consisting of *Salmonella* serovar *Heidelberg*, Hadar, *Enteritidis, Kentucky*, and *Dublin*.

3. The system according to claim 1, wherein the nucleotide sequence of one of the probes consists of the sequence shown in SEQ ID NO: 3.

4. A method for detecting *Salmonella* serovars in a sample, said method comprising: performing polymerase chain reaction (PCR) using an array for testing a sample simultaneously for a plurality of *Salmonella* serovars that are foodborne pathogens or food threat agents, said array comprising:
   two or more primer pairs placed on a microplate for receiving test samples, said two or more primer pairs being adapted to detect and distinguish with specificity DNA from at least two different *Salmonella* serovars that are foodborne pathogens or food threat agents,
   wherein all said primer pairs have similar melting temperatures such that they can be simultaneously run under the same polymerase chain reaction (PCR) conditions, and wherein said primer pairs comprise at least one primer selected from SEQ ID NO: 1 and SEQ ID NO: 2.

* * * * *

UNITED STATES PATENT AND TRADEMARK OFFICE
CERTIFICATE OF CORRECTION

| | | |
|---|---|---|
| PATENT NO. | : 11,447,834 B2 | |
| APPLICATION NO. | : 16/431039 | |
| DATED | : September 20, 2022 | |
| INVENTOR(S) | : Abebe et al. | |

It is certified that error appears in the above-identified patent and that said Letters Patent is hereby corrected as shown below:

On the Title Page

Item (72), Line 2, delete second inventor's last name "Aldhami" and insert --Aldahami--.

Signed and Sealed this
Twenty-third Day of January, 2024

*Katherine Kelly Vidal*

Katherine Kelly Vidal
*Director of the United States Patent and Trademark Office*

SEQUENCE LISTING

```
<160> NUMBER OF SEQ ID NOS: 127

<210> SEQ ID NO 1
<211> LENGTH: 20
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 1
gcagttcatt cgctttgtcg                                              20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cggaaaatac gtctcatgtc c                                            21

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
tagtccatca cccagcgcag tttc                                         24

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctggcatcaa gaatgtcgt                                               19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgcaaaaatc aggatggctc                                              20

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
tacggcgatt tctaccgtgt cgt                                          23

<210> SEQ ID NO 7
<211> LENGTH: 27
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 7
gatttacgac tgttggtgtt taagctg                                          27

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtgagaaatc cagataccag aaagaa                                           26

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
agaactacgc acggcaattt cga                                              23

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cggaaaatac gtctcatgtc c                                                21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gattcttcac gcacaatatc c                                                21

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aatctgaact tgagaaatca atcc                                             24

<210> SEQ ID NO 13
<211> LENGTH: 22
<212> TYPE: DNA
<213> ORGANISM: Artificial Sequence
<220> FEATURE:
```

<223> OTHER INFORMATION: Description of Artificial Sequence: Synthetic
       primer

<400> SEQUENCE: 13
ccgtgaggag attatttagc cc                                          22

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 14
acgttgagcg agtttatcgc t                                           21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 15
caatggtctg ttatggggaa                                             20

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 16
ctggcatcaa gaatgtcgt                                              19

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 17
cgcaaaaatc aggatggctc                                             20

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 18
gtgagaaatc cagataccag aaagaa                                      26

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
cgggatggtt taattatcaa tga                                          23

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gttgaatgga ggaagcgtcc                                              20

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccttgctgtg acactatgcc g                                            21

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cattagatat gaacaagcga ccg                                          23

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agtgcatttt caagccgtga g                                            21

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gagttttacc aactgatgtc ggg                                          23

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aactggcttg tttgattggc a                                            21

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
atgagtccaa tcgtgcctgc                                              20

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgaagtaaag ggtggaaaaa ggc                                          23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ggactattca ggatgctgtg aag                                          23

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gttggctacc ttggagcat                                               19

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgaggtcgcc aagttctgc                                               19

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 31
gacttgtcga tattgattca ggcg                                              24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ccacagcagt acatagaaag gacc                                              24

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aacgatgcct ttcagtcccg                                                   20

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aatctgtttg tctcctggca cc                                                22

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gcgaaatcat tgagggatag tg                                                22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ccgtgaggag attatttagc cc                                                22

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
```
aatctgaact tgagaaatca atcc                                          24

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ctggcatcaa gaatgtcgt                                                19

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cgcaaaaatc aggatggctc                                               20

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gattcttcac gcacaatatc c                                             21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cggaaaatac gtctcatgtc c                                             21

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
caatggtctg ttatggggaa                                               20

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
acgttgagcg agtttatcgc t                                              21

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cgtcagggaa aactgtattt aatcg                                          25

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ggatgctaag tgaagtgttg gg                                             22

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cgaccattgc actgattcat cat                                            23

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tacaaaatta gaacgacgag aagca                                          25

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48 acccttcaa tgttcctacg c                                               21

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tccagcagtt tgaagcactc                                                20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
agcggttctt ctacattgca                                              20

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gtccttattt tacgatgttt ccc                                          23

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ggaatgaact tgccaaggct                                              20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
attccagttg atcgcagagg                                              20

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
attcgatgac agcctgctga gct                                          23

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ttccagttga tcgcagagg                                               19

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gaatgaactt gccaaggctt                                              20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ctcaagacct ccagtgcctc                                              20

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ttaccagatg accgtatcac acc                                          23

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ctttcagttg ctgtacgtcc ct                                           22

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
attacgagca agtgagaggt cct                                          23

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 61
gaatttcagg aaagcctatg ccac                                         24

```
<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ttacgccctg ttacatcggt g                                              21

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tcccaaccct cgatcaac                                                  18

<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cattatcagt agggagtttt gtctgag                                        27

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tgatattgct aggctgttag tttg                                           24

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gtaaactcag atgtttcagg agaag                                          25

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
tttagaatgt agggttcttg gagta                                          25

<210> SEQ ID NO 68
```

<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
tcatttggca cttcaacacg g    21

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
gattgtactg actcaagatg gcg    23

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
ccagatcttc gcagggtcaa gct    23

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
gtgactgtcg gaatggaata agca    24

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
ggttcttaac gctgtaagca actc    24

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
atgaaattat ctgagcgaaa gca    23

<210> SEQ ID NO 74
<211> LENGTH: 22

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
tcacctatcg ctggtatagc ct                                           22

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
agcttggtca ggagttcttt ctc                                          23

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 76
gaaataaagc ctgtaagcgc gg                                           22

<210> SEQ ID NO 77
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
aattctacag tcagatagag tttcccc                                      27

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tgcgtcagat ttccttactc g                                            21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
acaatttaac accccctacc a                                            21

<210> SEQ ID NO 80
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 80
gaggttattt gaatctgccg t                                              21

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gaagagtatt tgccattgca aa                                             22

<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
caatatcaca gctaagaacc gtaaa                                          25

<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gtgaataatc ctcatcggtt cg                                             22

<210> SEQ ID NO 84
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gtgagtagtt taggcagcgt tatgg                                          25

<210> SEQ ID NO 85
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tagcttggca ttgggtcg                                                  18

<210> SEQ ID NO 86
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 86
ggttcaggcg gagattgtg                                                    19

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
acaacagaca tcactgaggg tgt                                               23

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gtggtgtcaa cggtaaagtt cag                                               23

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
cctgcactat cctcttcctc c                                                 21

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gctattggcc tgtctgatcc                                                   20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
ggacgcacag gtcaggtatg                                                   20

<210> SEQ ID NO 92
<211> LENGTH: 19
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 92
tgcaggaacc gtgataggg                                                    19

<210> SEQ ID NO 93
<211> LENGTH: 136
<212> TYPE: DNA
<213> ORGANISM: Salmonella enterica

<400> SEQUENCE: 93
gttgaatgga ggaagcgtcc aggttgaagg taattatggc attttgatgc tctataataa       60
ttcacaagcc accctgatgg gcaccgaggt caccgcaacg gcggaaacaa ctagcggcat      120
agtgtcacag caaggc                                                     136

<210> SEQ ID NO 94
<211> LENGTH: 188
<212> TYPE: DNA
<213> ORGANISM: Salmonella enterica

<400> SEQUENCE: 94
cattagatat gaacaagcga ccggactcaa ccgtattaaa gcgcatataa atactgctaa       60
caaattcacc cacatttatt ggcattggtg aattttttgg ttctttacgc tttccaattg      120
tcttggcttc aataactacc attctattta aaaaaccgt cccagcctca cggcttgaaa       180
atgcactc                                                              188

<210> SEQ ID NO 95
<211> LENGTH: 175
<212> TYPE: DNA
<213> ORGANISM: Salmonella enterica

<400> SEQUENCE: 95
agttttacca actgatgtcg gggctaaaac tgcaatatat aaattactcg ttagcgttcc       60
cttatatgac catctgccag aaattaaaga agccattgac gcaacggaaa acgccaatgc      120
taattcaggg caatatgttc tagtgttttc aatttgccaa tcaaacaagc cagtt          175

<210> SEQ ID NO 96
<211> LENGTH: 212
<212> TYPE: DNA
<213> ORGANISM: Salmonella enterica

<400> SEQUENCE: 96
atgagtccaa tcgtgcctgc gatactaata tatagatcgt ttttacttat ggtgtaattg       60
ctgatagcag ataagtatcg gagtctaaat acttaatcgt ggaaagattt acgcttccat      120
tttcgaagtc agtaactcta atatatggat gttctgttgc ggtattaagt aaagctttac      180
ctttgggaag ccttttttcca cccttttactt ca                                 212

<210> SEQ ID NO 97
<211> LENGTH: 111
<212> TYPE: DNA
<213> ORGANISM: Salmonella enterica

<400> SEQUENCE: 97
ggactattca ggatgctgtg aagttttgca gggagactgg aagacaagat gctggctcag       60
ccatggaggc atggaatgcc tgccgcaccg ccatgctcca aggtagccaa c              111

<210> SEQ ID NO 98
<211> LENGTH: 264
<212> TYPE: DNA
<213> ORGANISM: Salmonella enterica

<400> SEQUENCE: 98

| | | | | | |
|---|---|---|---|---|---|
| gacttgtcga | tattgattca | ggcgcagagg | atcattggaa | atattcaact | cagtgcataa | 60 |
| cacctgcatc | tggaaagacg | taccgtattg | agtctattcc | tctctacaca | gtctcgcaac | 120 |
| cagtaccagt | accagaacgc | gaacgtattc | gccgtgaaca | tgctgaatgg | tctgatgcca | 180 |
| cattcggcga | tgttggcccc | atcggtccac | tgaagcacct | ctcaaaagag | gcattggaaa | 240 |
| ctgccgcaga | acttggcgac | ctca | | | | 264 |

<210> SEQ ID NO 99
<211> LENGTH: 198
<212> TYPE: DNA
<213> ORGANISM: Salmonella enterica

<400> SEQUENCE: 99

| | | | | | |
|---|---|---|---|---|---|
| ccacagcagt | acatagaaag | gaccgggaga | accgcaaacg | tacttagaaa | ccttgactcg | 60 |
| ggcctgtcca | gcgtaaccag | cactgtcctc | aatgctatag | ccaactccac | atcaggtgct | 120 |
| gttgttggcg | gtgcaggtgg | agggattgct | ggcgctgctg | ccggggcgtt | ggctggagcg | 180 |
| ggactgaaag | gcatcgtt | | | | | 198 |

<210> SEQ ID NO 100
<211> LENGTH: 100
<212> TYPE: DNA
<213> ORGANISM: Salmonella enterica

<400> SEQUENCE: 100

| | | | | | |
|---|---|---|---|---|---|
| aatctgtttg | tctcctggca | cctataatat | cctctccatt | ttccacatct | tgttcatcta | 60 |
| tgttattaat | ggagtaaaca | ctatccctca | atgatttcgc | | | 100 |

<210> SEQ ID NO 101
<211> LENGTH: 354
<212> TYPE: DNA
<213> ORGANISM: Salmonella enterica

<400> SEQUENCE: 101

| | | | | | |
|---|---|---|---|---|---|
| aatctgaact | tgagaaatca | atccgtacag | cctatcttgc | cacaaatata | ctagcctatt | 60 |
| gggcaataca | agatggtaat | gcaaaacaag | ccctctatgt | atcggagcgt | tgcctgctat | 120 |
| gggtatggca | ccgtattcac | cttgaaaaaa | gtccacaaca | atacttctct | gccattaata | 180 |
| ttatatggca | aaactatatt | aatatctccg | cagaatactt | ttccaaactt | caaccctatt | 240 |
| ttcacgaaaa | atatcttctg | tcgtcatact | ctgccgatag | cgcattaatt | aatcttacta | 300 |
| tatttgaaca | aataggtata | ctctctacta | tcgggctaaa | taatctcctc | acgg | 354 |

<210> SEQ ID NO 102
<211> LENGTH: 325
<212> TYPE: DNA
<213> ORGANISM: Salmonella enterica

<400> SEQUENCE: 102

| | | | | | |
|---|---|---|---|---|---|
| ctggcatcaa | gaatgtcgtc | tcgtgctggc | cataggcagc | caaacgttca | gtttgacctg | 60 |
| acaatgtact | caactccagt | actcctccac | tgacaggatt | cccatagctg | tagctttgtt | 120 |
| tttcaacaaa | acaacgcgaa | ccatgctcag | ctgctccact | tggttcaaac | ctcgccctca | 180 |

```
cattcataaa aacgacacgg tagaaatcgc cgtacacgag cttatagatt tttgagatgg    240
gggtcaccac acttaaatta ttgctatttt gccctgtaca ctgcatccct gtcacaacat    300
tccatgagcc atcctgattt ttgcg                                          325
```

<210> SEQ ID NO 103
<211> LENGTH: 289
<212> TYPE: DNA
<213> ORGANISM: Salmonella enterica

<400> SEQUENCE: 103

```
cggaaaatac gtctcatgtc cgctcttctt tacgcagcaa agatgaaacc tttagaggtc     60
gcctcgaaga taacagtacc tatcagaaac tgcgctgggt gatggactac tggtgtgcgc    120
tatggttctg gccaatcgac aaagcgaatg aactgccgga tcgcggtatg tggctaatgg    180
agatggagac actgatcgac ggtattgtcg tcacggaaag agtcactgaa gttgcagagc    240
aggccaccgg caatctgttt gccgacgagg atattgtgcg tgaagaatc                289
```

<210> SEQ ID NO 104
<211> LENGTH: 246
<212> TYPE: DNA
<213> ORGANISM: Salmonella enterica

<400> SEQUENCE: 104

```
caatggtctg ttatggggaa aatcataaat attttttaaag agttgagagg cgggatttta     60
tttggtgaaa ggaacgacta cgctaaaatt tggcaagaaa ataccttc cacatctggg     120 gttgtttctg agtttgatga taatgtattt tcatcagcat atgattattg gcgttctctt    180
gaagggcctt ggagagaatt atttgtttgt ttttggaaca agttagcga taaactcgct    240 caacgt                                                               246
```

<210> SEQ ID NO 105
<211> LENGTH: 266
<212> TYPE: DNA
<213> ORGANISM: Salmonella enterica

<400> SEQUENCE: 105

```
tccctgacga caaaattcaa tccattgtac tcaggctatt attctgtgga aagactgaaa     60
cactaacagc cactttaat aaaaatttca aaaaattgt acccgttcat ttgcgaccg     120 aaatatcaaa ttttagaaat gactttacaa tgttgggata tttaacagaa aagactagtg    180
gatgggttac caagtttgtt gatttttcaa tcaacgaaat tgagaaaaac tcagcagaca    240
ttaaaggatt tcacgacgag tttagg                                         266
```

<210> SEQ ID NO 106
<211> LENGTH: 223
<212> TYPE: DNA
<213> ORGANISM: Salmonella enterica

<400> SEQUENCE: 106

```
ggtgagaata gcaagtcgta ctctgattac attaataaaa taaagaaat aactaaaaca     60 tctaagtacg gatataaaga gaaagttcta aactatgtta agtaggatt agatggtcaa    120 acatttcaga tcgatggtaa aaaactagaa attcaatcag atggaacaaa ttctttcaaa    180
tacattgaaa tatttctatc cctgttaata tcccttacaa gaa                      223
```

<210> SEQ ID NO 107

```
<211> LENGTH: 138
<212> TYPE: DNA
<213> ORGANISM: Salmonella enterica

<400> SEQUENCE: 107 acccttcaa  tgttcctacg  ctcaaaatgt  gatcgtgagc  tatatttgtc  actacatgaa     60
gattccgaat  tggatgctaa  ttcaatgcca  gtgcccttc   aggcgcgtcc  aggaatcgga    120
gtgcttcaaa  ctgctgga                                                     138

<210> SEQ ID NO 108
<211> LENGTH: 217
<212> TYPE: DNA
<213> ORGANISM: Salmonella enterica

<400> SEQUENCE: 108
agcggttctt  ctacattgca  gctagccaat  tttgatttag  cgattgcaat  ggcgaccgga     60
gatgtatcta  ttccccatgc  tgagagccct  aacgttcggg  ctgcaaacag  tgaagtcccc    120
cttccacaga  aagggtcgag  gataaccgga  gtgtcctttc  gatgttttt   tagcacttgg    180 taaggatact  caaggggaaa  catcgtaaaa  taaggac                              217

<210> SEQ ID NO 109
<211> LENGTH: 130
<212> TYPE: DNA
<213> ORGANISM: Salmonella enterica

<400> SEQUENCE: 109
gttccagttg  atcgcagagg  gacatgagtt  tatcaacacg  tgaaacaatt  cgcagttgct     60
cctggatagg  agctaattcg  atgacagcct  gctgagcttt  ttctgtacca  agccttggca    120
agttcattcc                                                                130

<210> SEQ ID NO 110
<211> LENGTH: 128
<212> TYPE: DNA
<213> ORGANISM: Salmonella enterica

<400> SEQUENCE: 110
ttccagttga  tcgcagaggg  acatgagttt  atcaacacgt  gaaacaattc  gcagttgctc     60
ctggatagga  gctaattcga  tgacagcctg  ctgagctttt  tctgtaccaa  gccttggcaa    120
gttcattc                                                                 128

<210> SEQ ID NO 111
<211> LENGTH: 368
<212> TYPE: DNA
<213> ORGANISM: Salmonella enterica

<400> SEQUENCE: 111
ctcaagacct  ccagtgcctc  gccaatccgc  ccaatccatg  ttcgaaccat  tttggcaagc     60
tcaacgagga  gcatccaatc  ttccattct   ggagcttcga  gcgttaccca  aagattaccc    120
tgcccctcat  atacacaggt  cagccgttgc  gcttcaagat  catcaattga  tgcgtagcac    180
ttgctctgac  gctcggtggg  aaagaaatct  tctgccgaag  gcctcatcac  tcgatgccat    240
ttaccattgt  tgtcactaat  gcgatgccgg  tcatatcctg  tgtctgccgc  tattcgtata    300
ccacggagta  aattcgtggg  aatcattaac  attagcgggt  gttccggtgt  gatacggtca    360
tctggtaa                                                                 368
```

```
<210> SEQ ID NO 112
<211> LENGTH: 381
<212> TYPE: DNA
<213> ORGANISM: Salmonella enterica

<400> SEQUENCE: 112
attacgagca agtgagaggt ccttacattc gataacgaga acttgattgc ggtctgagcg        60
ccaggcaaga agatcaatat cccccggatc acctggtaga ttcctgcgaa gaatttcagg       120
aaagcctatg ccacgtcgaa ctgtccagcc tatttcacga agttctctct ccaaagtttt       180
ttcgaatgtg tgtccttccc gcgctccacc taaccaagtg tctctcatac cctctgtgcg       240
aaagaagtca cgcttaaatt gcccagtgta tgcgccatcg aaaacgtatt taagggacag       300
attcaagagt cctggtgcga taacaattag tggatcgtga ctctcttcaa tctgtaacaa       360
gggacgtaca gcaactgaaa g                                                381

<210> SEQ ID NO 113
<211> LENGTH: 190
<212> TYPE: DNA
<213> ORGANISM: Salmonella enterica

<400> SEQUENCE: 113
tcccaaccct cgatcaacct gaactttgcg ttattgatgg caaagtcgtt acttcctcac        60
tggctgttgc cgattatttc cataagccac ataaagacgt actggctaag atttcccgcc       120
tggattgttc tgtcgaattt accgagcgaa atttctcgct cagcaaatac accgatgtaa       180
cagggcgtaa                                                              190

<210> SEQ ID NO 114
<211> LENGTH: 158
<212> TYPE: DNA
<213> ORGANISM: Salmonella enterica

<400> SEQUENCE: 114
tgatattgct aggctgttag tttgtgatgc ctggaaagca caggttaaag ggataccagc        60
cggttgtttt ctacttgcat tttacgatgg tgaagacggt gttgaagagg ctgtattgct       120
tagagcactt tctcagacaa aactccctac tgataatg                              158

<210> SEQ ID NO 115
<211> LENGTH: 414
<212> TYPE: DNA
<213> ORGANISM: Salmonella enterica

<400> SEQUENCE: 115
tttagaatgt agggttcttg gagtattta tagaacacag aaagggaata tagaatttgg         60
tgctgacctt gagaactttt atgcagctaa taattacact gtatacaaag ccaatagaga       120
tgttcttgaa tttatagtaa atcaacgaga tgatggcggt ttagttggtc aggactctga       180
atttaaaatt ggtagtgtaa gatattcatc tagccgtaga catcaatctc aagaggaaaa       240
tgttaatgta tgggtaaatc ctaaagattt tttaggaaaa aggtctgcta tgtttgggat       300
gacccgtact ggtaagtcga atactgtaaa gaaagtgata gaagcaacag aggaaatttc       360
aagaaaagct ttaatactat tggattcagc ttctcctgaa acatctgagt ttac             414

<210> SEQ ID NO 116
<211> LENGTH: 249
<212> TYPE: DNA
<213> ORGANISM: Salmonella enterica
```

<400> SEQUENCE: 116

| tcatttggca cttcaacacg gaagtgtgga cgcatatcgt tagttatatt gtcgtcagca | 60 |
| --- | --- |
| ataccagtgt cattgatcag ttcgatgcta ttaatcgcga tttgcgtatc cactttcact | 120 |
| gttaatggtg tggactggcg aatatttccc gcctcatctt ccaccgtcac ttgcagtgta | 180 |
| tagctgccat catcccacgt gctggcaggt gtaaataccc agttaccgcc atcttgagtc | 240 |
| agtacaatc | 249 |

<210> SEQ ID NO 117
<211> LENGTH: 95
<212> TYPE: DNA
<213> ORGANISM: Salmonella enterica

<400> SEQUENCE: 117

| ccagatcttc gcagggtcaa gctgtgtttg agtgagttca aaatagcgat caaccattga | 60 |
| --- | --- |
| gccgacaatc ttgcttattc cattccgaca gtcac | 95 |

<210> SEQ ID NO 118
<211> LENGTH: 423
<212> TYPE: DNA
<213> ORGANISM: Salmonella enterica

<400> SEQUENCE: 118

| ggttcttaac gctgtaagca actcaatatt aacggattca agatttcctt ctgcacgtag | 60 |
| --- | --- |
| aatctccaga caagcggcat acaaaattgt ctcagaatac ctgtattttg attcgcattg | 120 |
| cagagtcgca agctcgggaa gagtgggaac ctttgaagca ataaaatcca gacaatttct | 180 |
| taatgccccc cgaaccagtt tgtcgtcacc aaattctaat tcaattcttt ccggaagcat | 240 |
| gagcacaagt tctgcaaaac gcaccagaca accccagtga agacctcgtt ctacaatatc | 300 |
| tctgttttca ttaacgaatt ctatattttt ggcgtggatc tctcgttgcc ttctatcata | 360 |
| gcggttcatc tttcggctat gtctgaatct caagtgctgg tgctttcgct cagataattt | 420 |
| cat | 423 |

<210> SEQ ID NO 119
<211> LENGTH: 228
<212> TYPE: DNA
<213> ORGANISM: Salmonella enterica

<400> SEQUENCE: 119

| tcacctatcg ctggtatagc ctattattcc actagaatgc ataatgctaa taaaacacat | 60 |
| --- | --- |
| agatcaatca atgtagtatt accacctaaa gctacttaca aacagataat agctcaagaa | 120 |
| tattgcccgc gcttacaggc tttatttcat tttacacctc ctgtctcgtg gcaggttcta | 180 |
| aaaactttag actatcaatt tgtcggagaa agaactcctg accaagct | 228 |

<210> SEQ ID NO 120
<211> LENGTH: 349
<212> TYPE: DNA
<213> ORGANISM: Salmonella enterica

<400> SEQUENCE: 120

| aattctacag tcagatagag tttccccgcc ccttacactt gaatcagata tcgtgtcaga | 60 |
| --- | --- |
| ctttaaagaa cgatgcgagt actatatcga ttcccttaaa aaatatgaca agaaaacaa | 120 |
| taccaaaata aacttcgact taatgatcaa gcgaatttcg attatagtta atgggattac | 180 |
| aaaatgcctt gaagaatttt tgtctggaga tataaaatct gcttacgatg tatttaacga | 240 |

```
tattttttca tctagcacta ttaataaaca cataaggaga ataaccattc cccttttatga    300 tgtctgcaat gaaaaaagac ctttatttcg agtaaggaaa tctgacgca                349
```

<210> SEQ ID NO 121
<211> LENGTH: 132
<212> TYPE: DNA
<213> ORGANISM: Salmonella enterica

<400> SEQUENCE: 121

```
acaatttaac accccctacc aagggattta cctaaagcct tttgaatttt tttaacttct     60
ctcgctctat ctaaacgatt aaagttttca aatagacttt cttttacctt aacggcagat    120
tcaaataacc tc                                                        132
```

<210> SEQ ID NO 122
<211> LENGTH: 288
<212> TYPE: DNA
<213> ORGANISM: Salmonella enterica

<400> SEQUENCE: 122

```
caatatcaca gctaagaacc gtaaataatg catccgaagg gatgcgcatt ctagttaagg     60
catatattca agggacgaat atcggaggtg gtgaattcag ttggaactcc acaaccactc    120
aagctgatga tggcgggtac atcattaggc caactggaat tgttactggc gcctggatta    180
gaatcagcaa aacaagcaag gtttatctga ctgagtatgg ggcaaccggc gatgataccg    240
acgtatcaac taagatatca tctgtttttg caatggcaaa tactcttc                 288
```

<210> SEQ ID NO 123
<211> LENGTH: 256
<212> TYPE: DNA
<213> ORGANISM: Salmonella enterica

<400> SEQUENCE: 123

```
gtgaataatc ctcatcggtt cgcaataatt ggtattgata cccttcaagg acaagctctc     60
tcgccagtct atgctgatcg ggttgttgtg aagcaaaatc tctccctaac actctattct    120
ggaaattatt agctctggtt attgcattag catttagatc attttcatca ttattaattt    180
caatgaaacg aacagggact ttaacttgat aaattctatc tcctagcaca tccataacgc    240
tgcctaaact actcac                                                    256
```

<210> SEQ ID NO 124
<211> LENGTH: 315
<212> TYPE: DNA
<213> ORGANISM: Salmonella enterica

<400> SEQUENCE: 124

```
tagcttggca ttgggtcgtc tgttaatcat taaatcagaa cgtgtaaata tcttttccca     60
aagctcttta aactctttta ttttttcatt ttgaacaagt cttggtgtct cggataaaaa    120
atctttaatg ccataaataa aattaccaag ttgagcacca tcgaaggatg aactggtttt    180
tgattgaatg aatgttatat ctacatctaa atagctgtaa ttattagcga tatcatcaaa    240
cgcttcgata gaagttataa tccttccgtt aatggaaata actaatccat ctatagcaca    300
atctccgcct gaacc                                                     315
```

<210> SEQ ID NO 125
<211> LENGTH: 101
<212> TYPE: DNA

```
<213> ORGANISM: Salmonella enterica

<400> SEQUENCE: 125
gtggtgtcaa cggtaaagtt cagcgtccgc gtcgccgtgt tccctgcgat atcggtcgct      60
tccaccgtca gcgtgtgtac accctcagtg atgtctgttg t                        101

<210> SEQ ID NO 126
<211> LENGTH: 335
<212> TYPE: DNA
<213> ORGANISM: Salmonella enterica

<400> SEQUENCE: 126
gctattggcc tgtctgatcc agagtgtagt tctcttcttt caggtctaaa tacttcgttt      60
gtttcgcgta tatggaacga caaaaaaatc acagctcacc atggcattat ccctacccga    120
aacgcgttta agttttctgc gttaagtgag gcagagcgaa gggtatacac ccttatccgc    180
cgaaattatc tggcacaatt tcttcccctg cacgaatctg atattactcg tctgcagttt    240
gacattggcg ggcaactgtt ccgcacaaca ggaaggacgg agattgtaat gggctggaag    300
gtccttttca gtaaggagga agaggatagt gcagg                                335

<210> SEQ ID NO 127
<211> LENGTH: 163
<212> TYPE: DNA
<213> ORGANISM: Salmonella enterica

<400> SEQUENCE: 127
ggacgcacag gtcaggtatg taaaagcagc cgcagcagca ataacgactg cccacccagc      60
ccacttcggc caggcgccat ctgttggctc cggaacggcc acatccgctt caaatccggc    120
cagtgccgca tccagcaccg ccccccctat cacggttcct gca                      163
```